(12) United States Patent
Leighton

(10) Patent No.: US 9,149,474 B2
(45) Date of Patent: Oct. 6, 2015

(54) COMPOSITIONS AND METHODS FOR TREATING SYMPTOMS OF INFLAMMATORY RELATED CONDITIONS USING A COMBINATION OF AN ANTIHISTAMINE AND A STIMULANT

(76) Inventor: Michael Leighton, Holland, PA (US)

( * ) Notice: Subject to any disclaimer, the term of this patent is extended or adjusted under 35 U.S.C. 154(b) by 5 days.

(21) Appl. No.: 13/465,016

(22) Filed: May 6, 2012

(65) Prior Publication Data

US 2013/0131026 A1 May 23, 2013

Related U.S. Application Data

(60) Provisional application No. 61/563,271, filed on Nov. 23, 2011.

(51) Int. Cl.

| | |
|---|---|
| *A61P 7/10* | (2006.01) |
| *A61P 9/00* | (2006.01) |
| *A61P 19/02* | (2006.01) |
| *A61P 11/06* | (2006.01) |
| *A61P 11/08* | (2006.01) |
| *A61P 39/06* | (2006.01) |
| *A61P 35/00* | (2006.01) |
| *A61P 37/08* | (2006.01) |
| *A61K 31/495* | (2006.01) |
| *A61P 29/00* | (2006.01) |
| *A61K 31/522* | (2006.01) |
| *A61K 31/56* | (2006.01) |
| *A61K 45/06* | (2006.01) |

(52) U.S. Cl.
CPC ............ *A61K 31/495* (2013.01); *A61K 31/522* (2013.01); *A61K 31/56* (2013.01); *A61K 45/06* (2013.01)

(58) Field of Classification Search
CPC ............ A61K 2300/00; A61K 31/495; A61K 31/522; A61K 31/56; A61K 45/06
USPC ............................................ 514/171, 263.34
See application file for complete search history.

(56) References Cited

U.S. PATENT DOCUMENTS 5,541,210 A * 7/1996 Cupps et al. .................. 514/394
2004/0259809 A1 12/2004 Gonzales

FOREIGN PATENT DOCUMENTS

WO WO95/07079 A1 3/1995

OTHER PUBLICATIONS

Shapiro (Caffeine for Allergic Rhinitis, The Lancet, Apr. 3, 1992, p. 793).*
International Preliminary Report on Patentability application No. PCT/US2013/039348 issued by the International Bureau of WIPO, Geneva, Switzerland, dated Nov. 20, 2014.
International Search Report (ISR) and Written Opinion for International Application No. PCT/US2013/039348, International Filing Date May 2, 2013, Date of Mailing ISR Oct. 22, 2013, 12 pages, United States Patent Office, Alexandria, Virginia.

* cited by examiner

*Primary Examiner* — Kathrien Cruz
(74) *Attorney, Agent, or Firm* — Peter B. Scull; Hamilton, DeSanctis & Cha, LLP

(57) ABSTRACT

The present invention relates to compositions containing stimulant and anti-histamine compounds, to methods for treating symptoms related to inflammation using the combination compounds, and to a method for preparing the compositions.

5 Claims, No Drawings

COMPOSITIONS AND METHODS FOR TREATING SYMPTOMS OF INFLAMMATORY RELATED CONDITIONS USING A COMBINATION OF AN ANTIHISTAMINE AND A STIMULANT

PRIORITY

This nonprovisional patent application claims priority to U.S. 61/563,271, filed 23 Nov. 2011, and which application is entirely incorporated herein by reference.

FIELD OF THE PRESENT INVENTION

The present invention relates to compositions containing a combination of stimulant and anti-histamine compounds, to methods for treating symptoms related to inflammation using the combination compounds, and to a method for preparing the compositions.

BACKGROUND OF THE PRESENT INVENTION

Inflammation often is a bodily response to infection or injury in which cells involved in detoxification and repair are mobilized to the compromised site by inflammatory mediators. The infection or injury can be a result of acute or chronic disease, disorders, conditions or trauma, environmental conditions, or aging. Examples of diseases, disorders, including autoimmune disorders, conditions, including environmental conditions, or trauma, in which inflammation plays, or is thought to play a role, include diseases, disorders, syndromes, conditions and injuries of the cardiovascular, digestive, integumentary, muscular, nervous, reproductive, respiratory and urinary systems, as well as, diseases, disorders, syndromes, conditions and injuries of tissue and cartilage such as atherosclerosis, Irritable Bowel Syndrome (IBS), psoriasis, tendonitis, Alzheimer's disease and vascular dementia, multiple sclerosis, diabetes, endometriosis, asthma and kidney failure.

Thus, there is a need for compositions that treat symptoms associated with inflammation that potentially lacks the side effects of known treatments.

SUMMARY OF THE PRESENT INVENTION

It now has been found that compositions comprising at least one stimulant and at least one anti-histamine provide unexpected degrees of improvement of symptoms associated with inflammation over the effects of either compound alone. Without being bound by any particular theory, the treatment of symptoms related to or associated with inflammation can be the unexpected or synergistic result of the ability of the combination of stimulant and anti-histamine compounds to modulate the effects of one or more of TNF-α, IL-1β, IL-12, and IL-10, and/or pathways associated therewith. The present invention, therefore, is directed to compositions and uses of stimulant and anti-histamine compounds for treating symptoms associated with inflammation, and for other unmet needs.

The present invention provides a composition for treating symptoms associated with inflammation comprising:

at least one stimulant compound and at least one anti-histamine compound, and a pharmaceutically acceptable carrier or diluent; and optionally, an additional active ingredient.

The present invention further provides a composition for promoting healthy joints comprising:

at least one stimulant and at least one anti-histamine compound or a pharmaceutically acceptable salt thereof;

a carrier; and optionally, an additional active ingredient.

In some embodiments, the composition of the present invention is administered by a route selected from oral, buccal, cutaneous, nasal, parenteral, vaginal and rectal.

In preferred embodiments, the stimulant is caffeine or a derivative thereof and the anti-histamine is selected from loratadine, fexofenadine, levocetirizine dihydrochloride, 4-(4-(bis(4-fluorophenyl)methyl)piperazin-1-ylbut-2-enyloxy)acetic acid (SUN-1334H), and/or cetirizine.

In some embodiments, the inflammation treated by the method of the present invention is associated with one or more of relief of symptoms associated with one or more of allergic rhinitis, chronic sinusitis, seasonal rhinitis, seasonal allergic rhinitis, urticaria, chronic idiopathic urticarial, atopic dermatitis, perennial allergic rhinitis, acute nasal & sinus congestion, chronic nasal & sinus congestion, exercise induced asthma, exercise induced bronchospasm, chronic asthma, and/or seasonal asthma.

In some embodiments, the inflammation that the composition of the present invention treats symptoms thereof is associated with a joint condition, an inflammation of the airways, or an inflammatory bowel disease. In some such embodiments, the joint condition comprises an arthritis or a joint injury. In some such embodiments, the inflammation of the airways comprises an asthma or chronic obstructive pulmonary disease. In some such embodiments, the asthma is chronic. In some such embodiments, the chronic obstructive pulmonary disease comprises chronic bronchitis and emphysema. In some such embodiments, the chronic obstructive pulmonary disease comprises chronic bronchitis. In some such embodiments, the inflammatory bowel disease comprises ulcerative colitis and Crohn's disease. In some such embodiments, the inflammatory bowel disease comprises ulcerative colitis. In some such embodiments, the inflammatory bowel disease comprises Crohn's disease.

In some embodiments, the at least one stimulant and at least one anti-histamine composition of the composition of the present invention is contained within a botanical extract. In some embodiments, the at least one stimulant and at least one anti-histamine composition of the composition of the present invention is contained within a microbial extract.

In some embodiments, the additional active ingredient of the composition of the present invention is selected from a group consisting of a protective agent, a demulcent, an emollient, an astringent, a steroidal anti-inflammatory agent, a non-steroidal anti-inflammatory agent, an antioxidant, a chemotherapeutic agent, an additional antihistamine agent and a cleansing agent.

In some embodiments, the composition of the present invention comprises a mixture selected from the group consisting of a solution, an emulsion, a suspension and a powder.

In some embodiments, the composition of the present invention comprises a mixture of isomers or enantiomers at various ratios or singly, e.g., but not limited to, levo and/or dextro enantiomers or stereoisomers, separated or purified or synthesized as one or more isomers for one or more active ingredients, e.g., but not limited to at least one stimulant and/or at least one anti-histamine.

In some embodiments, the stimulant and anti-histamine compound of the composition of the present invention comprises from about 0.01% to about 50% w/w of the composition. In some embodiments, the stimulant and anti-histamine compound comprises from about 0.01% to about 5% w/w of the composition.

The present invention further provides a method of treating symptoms associated with inflammation in a mammal in need thereof, the method comprising administering to the mammal a pharmaceutically effective amount of a composition comprising:

at least one stimulant and at least one anti-histamine composition or a pharmaceutically acceptable salt thereof;

a carrier; and optionally, an additional active ingredient.

In preferred embodiments, the stimulant is caffeine or a derivative and the anti-histamine is selected from loratadine, fexofenadine, levocetirizine dihydrochloride, 4-(4-(bis(4-fluorophenyl)methyl)piperazin-1-ylbut-2-enyloxy)acetic acid, and/or cetirizine.

In some embodiments, the inflammation treated by the method of the present invention is associated with one or more of relief of symptoms associated with one or more of allergic rhinitis, chronic sinusitis, seasonal rhinitis, seasonal allergic rhinitis, urticaria, chronic idiopathic urticarial, atopic dermatitis, perennial allergic rhinitis, acute nasal & sinus congestion, chronic nasal & sinus congestion, exercise induced asthma, exercise induced bronchospasm, chronic asthma, and/or seasonal asthma.

In some embodiments, the inflammation treated by the method of the present invention is associated with a joint condition, an inflammation of the airways or an inflammatory bowel disease.

In some such embodiments, the joint condition comprises an arthritis or a joint injury. In some such embodiments, the composition of the method of the present invention for treating inflammation further comprises a penetration enhancer.

In some embodiments of the method of the present invention, the inflammation of the airways comprises an asthma or a chronic pulmonary obstructive disease.

In some embodiments of the method of the present invention, the inflammation is associated with an inflammatory bowel disease.

In some embodiments of the methods, the inflammation is associated with motion sickness or nausea, e.g., but not limited to, nausea due to a variety of causes, including, e.g., travel (motion sickness), pregnancy (e.g., morning sickness), anesthesia (e.g., post-operative) or chemotherapy.

In some embodiments of the method of the present invention the composition is administered by a route that is oral, buccal, parenteral, nasal, vaginal or rectal.

The present invention further provides a kit comprising a composition for treating or preventing inflammation, or for promoting healthy joints, the kit comprises: a composition comprising:

at least one stimulant and at least one anti-histamine composition or a pharmaceutically acceptable salt thereof;

a carrier, and optionally, an additional active ingredient.

In preferred embodiments, the stimulant is caffeine or a derivative thereof and the anti-histamine is selected from loratadine, fexofenadine, levocetirizine dihydrochloride, 4-(4-(bis(4-fluorophenyl)methyl)piperazin-1-ylbut-2-enyloxy)acetic acid, and/or cetirizine.

In some embodiments, the kit of the present inventions further comprises a plurality of individual dosage units of the composition and a plurality of needles. In some embodiments, the plurality of individual dosage units and the plurality of needles of the kit of the present invention provides for an administration regimen selected from the group consisting of daily, weekly and monthly.

DETAILED DESCRIPTION OF THE PRESENT INVENTION

It now has been found that compositions comprising at least one stimulant and at least one anti-histamine provide unexpected degrees of improvement of symptoms associated with inflammation over the effects of either compound alone or additively. Without being bound by any particular theory, the treatment of symptoms related to or associated with inflammation can be the unexpected or synergistic result of the ability of the combination of stimulant and anti-histamine compounds to modulate the effects of one or more of TNF-$\alpha$, IL-1$\beta$, IL-12, and IL-10, and/or associated inflammatory pathways. The present invention, therefore, is directed to compositions and uses of stimulant and anti-histamine compounds for treating symptoms associated with inflammation, and for other unmet needs.

In one aspect, the present invention provides compositions having a stimulant and anti-histamine compound, for example and without limitation, the stimulant is caffeine or a derivative and the anti-histamine is selected from loratadine, fexofenadine, levocetirizine dihydrochloride, and 4-(4-(bis(4-fluorophenyl)methyl)piperazin-1-ylbut-2-enyloxy)acetic acid (SUN-1334H), and/or cetirizine (hereinafter, "C/L, F, LD, SUN or C") for treating, or preventing, inflammation, or for promoting overall health of the various anatomical systems and their related joints, tissues, and organs. The compositions of the present invention can be employed usefully in pharmaceutical compositions.

In some embodiments, the composition of the present invention is used to treat symptoms associated or related to inflammation. As used herein, "treating," "treat" or "treatment" includes abrogating, substantially inhibiting, slowing or reversing the progression of a condition, substantially ameliorating clinical or aesthetical symptoms of a condition, protecting from harmful or annoying stimuli, or generally promoting health. In some embodiments, the inflammation treated by the method of the present invention is associated with one or more of relief of symptoms associated with one or more of allergic rhinitis, chronic sinusitis, seasonal rhinitis, seasonal allergic rhinitis, urticaria, chronic idiopathic urticarial, atopic dermatitis, perennial allergic rhinitis, acute nasal & sinus congestion, chronic nasal & sinus congestion, exercise induced asthma, exercise induced bronchospasm, chronic asthma, and/or seasonal asthma.

In some embodiments, the composition of the present invention is used to promote healthy joints. As used herein, "promoting," "promote" or "promotion" includes contributing to, furthering, helping or maintaining the progression and/or growth of a joint.

As used herein the term "inflammation" refers to a physiologic response to infection and injury in which cells involved in detoxification and repair are mobilized to the compromised site by inflammatory mediators. The classic signs of inflammation can be one or more of pain (dolor), heat (calor), redness (rubor), swelling (tumor), and loss of function (functio laesa). Histologically, inflammation can involve one or more of a complex series of events, including dilatation of arterioles, capillaries and venules, with increased permeability and blood flow; exudation of fluids, including plasma proteins; and leukocytic migration into the inflammatory focus.

The term "acute inflammation," as used herein, refers to inflammation, usually of sudden onset, characterization by the classical signs, with predominance of the vascular and exudative processes. The term "chronic inflammation," as used herein, refers to inflammation of slow progress and marked chiefly by the formation of new connective tissue; it may be a continuation of an acute form or a prolonged low-grade form, and usually causes permanent tissue damage.

Regardless of the initiating agent, the physiological changes accompanying acute inflammation can encompass one of more of four features: (1) vasodilation, which results in a net increase in blood flow, is one of the earliest physical responses to acute tissue injury; (2) in response to inflammatory stimuli, endothelial cells lining the venules contract, widening the intracellular junctions to produce gaps, leading to increased vascular permeability, which permits leakage of plasma proteins and blood cells out of blood vessels; (3) a strong infiltration of leukocytes at the site of inflammation, particularly neutrophils, which promote tissue damage by releasing toxic substances at the vascular wall or in uninjured tissue; and (4) fever, produced by pyrogens released from leukocytes in response to specific stimuli.

During the inflammatory process, soluble inflammatory mediators of the inflammatory response work together with cellular components in a systemic fashion in the attempt to contain and eliminate the agents causing physical distress. The term "inflammatory mediators," as used herein, refers to the molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, proinflammatory cytokines, including, but not limited to, IL-1β, IL-10, interleukin-1, interleukin-4, interleukin-6, interleukin-8, tumor necrosis factor (TNF), interferon-gamma.

Inflammation can result from a wide variety of diseases, conditions, syndromes, disorders, injuries and the like of the various anatomical systems, including, and without limitation, those of the:

(1) skeletal system including, but not limited to, such diseases, conditions, syndromes, disorders, and injuries, such as (a) arthritis, including, but not limited to, psoriatic arthritis, osteoarthritis, rheumatoid arthritis, juvenile rheumatoid arthritis, juvenile psoriatic arthritis, and Gouty arthritis, (b) soft tissue rheumatic diseases, which are rheumatic diseases that affect the tissues and structures that surround a joint and produce pain, swelling or inflammation, such as tendonitis, bursitis, and myofascial syndrome, (c) Reiter's syndrome, a triad of disorders that can appear consecutively or concurrently that include inflammation of the urethra, the iris and ciliary body, and the joints (d) Paget's disease, a metabolic bone disease that involves bone destruction and regrowth which results in deformity, (e) Still's disease, in adults, an illness with fever, rash, and joint pain, which can lead to chronic arthritis; it is more common in children, where it is called systemic juvenile rheumatoid arthritis, (f) sarcoidosis, an immune system disorder characterized by non-necrotizing granulomas (small inflammatory nodules) that can affect any organ, though the lungs and lymph nodes appear most often affected, (g) Marfan syndrome, a connective tissue multisystemic disorder characterized by skeletal changes (arachnodactyl), long limbs, joint laxity, pectus), cardiovascular defects (aortic aneurysm which may dissect, mitral valve prolapse), and ectopia lentis (h) Lyme disease, an inflammatory disorder caused by infection with *Borrelia burgdorferi*, a nonpyogenic spirochete, (i) lupus, any of several forms of ulcerative skin diseases, including, e.g., systemic lupus erythematosus (SLE) and juvenile SLE, (j) gout. (k) polymyalgia rheumatica, a syndrome within the group of collagen diseases involving pain and stiffness in the hip or shoulder area, (l) fibromyalgia, (m) Ehlers-Danlos syndrome, a group of inherited disorders of the connective tissue, occurring in at least ten types, I to X, based on clinical, genetic, and biochemical evidence, varying in severity from mild to lethal, and often characterized by hyperelasticity and fragility of the skin, hypermobility of the joints, and fragility of the cutaneous blood vessels, (n) dermatomyositis, a connective-tissue disease that is characterized by inflammation of the muscles and the skin, (O) polymyositis, a chronic, progressive inflammatory disease of skeletal muscle, (p) scleroderma, a chronic hardening and thickening of the skin, a finding in various different diseases, occurring in a localized or focal form as well as a systemic disease, (q) spondyloartropathy, any of several diseases affecting the joints of the spine such as ankylosing spondylitis, (r) Behçet's disease, a chronic condition that causes canker sores or ulcers in the mouth and on the genitals, and inflammation in parts of the eye, (s) avascular necrosis, a disease resulting from the temporary or permanent loss of the blood supply to the bones, (t) psoriasis, (u) skin cancer, and (v) bone cancer, (2) the respiratory system, including, but not limited to, such diseases, conditions, syndromes, disorders, and injuries such as (a) asthma, including, without limitation, chronic, atopic, allergic, baker's, bronchial, bronchitic, cardiac, cat, colophony, cough variant, exercise-induced, intrinsic, miller's, nasal, and occupational asthma (b) chronic obstructive pulmonary disease, including, e.g., chronic bronchitis and emphysema, (c) pneumonia, (d) tuberculosis, and (e) lung cancer;

(3) the digestive system, including, but not limited to, such diseases, conditions, syndromes, disorders, and injuries such as (a) inflammatory bowel disease including Crohn's disease and ulcerative colitis, (b) eosinophilic disorder, a condition where high numbers of eosinophils cause inflammation of the digestive tract, (c) gastritis, inflammation and irritation of the stomach, (d) hepatitis, inflammation and irritation of the liver, (e) cholecystitis, inflammation and irritation of the gallbladder, (g) pancreatitis, inflammation and irritation of the pancreas, (h) periodontal disease, (i) gastric cancer, (j) liver cancer, (k) colorectal cancer, (l) pancreatic cancer; (m) inflammation is associated with motion sickness or nausea, e.g., but not limited to, nausea due to a variety of causes, including, e.g., travel (motion sickness), pregnancy (e.g., morning sickness), anesthesia (e.g., post-operative) or chemotherapy.

(4) the cardiovascular system, including, but not limited to, such diseases, conditions, syndromes, disorders, and injuries such as (a) atherosclerosis, (b) coronary heart disease, and (c) ischemia;

(5) the cerebrovascular system, including, but not limited to, such diseases, conditions, syndromes, disorders, and injuries such as (a) stroke;

(6) the nervous system, including, but not limited to, such diseases, conditions, syndromes, disorders, and injuries such as (a) Alzheimer's disease, (b) vascular dementia, (c) Parkinson's disease, (d) Huntington's disease, (e) amyotrophic lateral sclerosis, (f) multiple sclerosis, and (g) traumatic brain injury; and (7) the reproductive system, including, but not limited to, such diseases, conditions, syndromes, disorders, and injuries such as (a) endometrial cancer, (b) prostate cancer, (c) cervical cancer, (d) ovarian cancer, (e) breast cancer, (f) breast inflammation, (g) endometriosis, (h) prostatitis, inflammation of the prostate gland, (i) penile inflammation, (j) epididymitis, inflammation of the epididymis (a duct of the sperm canal), (k) bartholinitis, an inflammation of Bartholin's duct, (l) vaginitis, (m) salpingitis, inflammation of the oviduct (Fallopian tubes), (n) cervicitis, inflammation of the cervix, (o) oophoritis, inflammation of the ovary, and (p) pelvic inflammatory disease (PID), an infection of the female reproductive system, of which vaginitis, cervicitis, salpingitis, and oophoritis are subsets.

The body's response to inflammation can include various symptoms, including edema, vasodilation, fever and pain, amongst others. For example, when inflammation is localized to joints, swelling of the joint lining, wearing down of cartilage and stiffening of the joints may occur. Thus, inflammation involving joints can be linked to a wide range of underlying joint conditions, from sprains to conditions collectively referred to as "arthritis," including rheumatoid arthritis. Such inflammation often is associated with autoimmune disorders.

When inflammation is localized to the lungs, symptoms such as swelling and narrowing of the lining of the airways (i.e., bronchial tubes, bronchi) may occur, resulting in constriction of the airways. The inflammation can stimulate production of mucous (sputum), which can cause further obstruction of the airways. Inflammation of the airways is associated with a number of diseases, disorders and conditions. For example, allergic asthma, a disease linked to inflammation of the airways, is thought to be caused by an exaggerated response of the immune system to harmless allergens (e.g., the house dust mite) resulting in a typical infiltration of the airway walls and injury and desquamation of the airway epithelium by e.g., activated eosinophils and lymphocytes. Other types of asthma are provoked by factors including, but not limited to, vigorous exercise, irritant particles, and psychologic stresses. While asthma often is chronic, the inflammation of the airways and resultant obstruction of air flow to the lungs in asthma often is reversible. In contrast, chronic obstructive pulmonary disease (COPD), also known as chronic obstructive lung disease (COLD), which also results in obstruction of air flow to the lungs, is unlike asthma because the obstruction often is not reversible, i.e., it is permanent, and often progressive. COPD includes primarily chronic bronchitis and emphysema.

The term, "inflammatory bowel disease" (also known as Irritable Bowel Syndrome or IBS) often refers to two chronic diseases that cause inflammation of the intestines: ulcerative colitis and Crohn's disease. In ulcerative colitis (an inflammatory disease of the large intestine, i.e., the colon), the inner lining—or mucosa—of the intestine is inflamed (i.e., the lining of the intestinal wall reddens and swells) and develops ulcers. Ulcerative colitis often is most severe in the rectal area. In contrast, Crohn's disease (an inflammatory disease of the small intestine) usually involves the lower part of the small intestine, called the ileum, but it can affect any part of the digestive tract, from the mouth to the anus. In Crohn's disease, the inflammation extends deep into the lining of the affected organ, which can cause pain and make the intestines empty frequently, resulting in diarrhea and other digestive conditions.

Inflammation also has been shown to play a role in cardiovascular diseases, disorders and conditions. Inflammation of the heart (myocarditis) may result in symptoms such as shortness of breath or fluid retention. In atherosclerosis, the process in which fatty deposits build up in the lining of arteries that can contribute to heart attack and stroke, it is believed that the inner layer of arteries become injured by high blood pressure, tobacco smoke, diabetes, or high levels of triglycerides and cholesterol, thereby triggering an inflammatory response. The inflamed artery lining traps fats, cholesterol, blood platelets, calcium and cellular waste, resulting in the production of plaque. An accumulation of plaque can restrict blood flow through the artery, and rupturing plaque can cause blood clots that block blood flow through the artery. Such blood clots also can break loose, travel to the heart and cause a heart attack, or travel to the brain and cause a stroke. C-reactive protein (CRP) is one of the acute phase proteins that increase during inflammation. It has been suggested that testing the CRP level in blood of an individual may be used to assess cardiovascular disease risk.

In the urinary system, inflammation of the kidneys (nephritis) has been associated with high blood pressure and kidney failure. Nephritis has been linked to various diseases, disorders and conditions such as kidney disease, kidney stones, kidney cancer, gout, Sjogren's Syndrome (an autoimmune disease damaging the eye tear ducts and other glands), lupus, yellow fever and typhoid fever.

Inflammation also has been implicated in various cancers. A genetic link between cancer and inflammation has been discovered that the proinflammatory gene I-kappa-B kinase (IKK beta) acts differently in two cell types to initiate cancer, and that deletion of that gene in mice decreased both the incidence of cancer and tumor growth. Strong support for a link between inflammation and cancer, including prostate cancer, breast cancer, ovarian cancer, cervical cancer, colon cancer and pancreatic cancer Inflammation plays a role in certain cutaneous diseases which can also be treated by a method of an present invention. Atopic dermatitis (AD) is a pruritic disease of unknown origin that usually starts in early infancy (an adult-onset variant is recognized); it is characterized by pruritus, eczematous lesions, xerosis (dry skin), and lichenification (thickening of the skin and an increase in skin markings). Atopic dermatitis may be associated with other atopic (immunoglobulin E [IgE]) diseases (eg, asthma, allergic rhinitis, urticaria, acute allergic reactions to foods). Atopic dermatitis has enormous morbidity, and the incidence and prevalence appear to be increasing. Other conditions with different etiologies and prognoses are often grouped under the umbrella of a diagnosis of atopic dermatitis.

Good evidence indicates that genetic factors are important in the development of atopic dermatitis, but the pathophysiology is still poorly understood. Two main hypotheses have been proposed regarding the development of the inflammatory lesions. The first suggests an immune dysfunction resulting in IgE sensitization and a secondary epithelial-barrier disturbance. The second proposes a defect in epithelial cells leading to the defective barrier problem, with the immunological aspects being epiphenomena.

In healthy individuals, balance exists between 2 important subdivisions of T cells (ie, $T_H1$, $T_H2$). The immune hypothesis invokes an imbalance in the T lymphocytes, with $T_H2$ cells predominating; this results in cytokine production of interleukins 4, 5, 12, and 13 and granulocyte macrophage colony-stimulating factor, causing an increase in IgE and lowered interferon gamma levels. Later, in persons with chronic atopic dermatitis, the $T_H1$-type cells predominate. Other cell types are also involved in the process, including eosinophils, Langerhans cells, keratinocytes, and B cells.

The second hypothesis involves defective barrier function in the stratum corneum of Atopic dermatitis patients, leading to the entry of antigens that result in the production of inflammatory cytokines. Some authors question whether the antigens can also be absorbed from the gut (eg, from food) and the lungs (eg, from house dust mites). Xerosis is known to be an associated sign in many atopic dermatitis patients. Evidence has shown multiple loss-of-function mutations in the filaggrin gene (FLG) on band 1q21.3 in patients with atopic dermatitis in Europe and other filaggrin mutations in Japanese patients. This gene is mutated in persons with ichthyosis vulgaris; it is associated with early-onset atopic dermatitis and with airway disease in the setting of atopic dermatitis. These changes are only found in 30% of European patients, begging the question of whether other genetic variants may also be responsible for some of the findings in the pathogenesis of atopic dermatitis.

In atopic dermatitis, transepidermal water loss is increased. Defective lamellar bodies may be caused by abnormalities of ceramide production. Whether the inflammation causes primary or secondary epidermal barrier breakdown is not known, but with the knowledge that filaggrin is involved in epithelial disruption, it is now thought that this finding leads to increased transepidermal penetration of environmental allergens, increasing inflammation and sensitivity.

Rhinitis is defined as inflammation of the nasal membranes and is characterized by a symptom complex that consists of any combination of the following: sneezing, nasal congestion, nasal itching, and rhinorrhea.[2] The eyes, ears, sinuses, and throat can also be involved. Allergic rhinitis is the most common cause of rhinitis. It is an extremely common condition, affecting approximately 20% of the population.

Although allergic rhinitis is not a life-threatening condition, complications can occur and the condition can significantly impair quality of life, which leads to a number of indirect costs. Allergic rhinitis involves inflammation of the mucous membranes of the nose, eyes, eustachian tubes, middle ear, sinuses, and pharynx. The nose invariably is involved, and the other organs are affected in certain individuals. Inflammation of the mucous membranes is characterized by a complex interaction of inflammatory mediators but ultimately is triggered by an immunoglobulin E (IgE)-mediated response to an extrinsic protein.

The tendency to develop allergic, or IgE-mediated, reactions to extrinsic allergens (proteins capable of causing an allergic reaction) has a genetic component. In susceptible individuals, exposure to certain foreign proteins leads to allergic sensitization, which is characterized by the production of specific IgE directed against these proteins. This specific IgE coats the surface of mast cells, which are present in the nasal mucosa. When the specific protein (eg, a specific pollen grain) is inhaled into the nose, it can bind to the IgE on the mast cells, leading to immediate and delayed release of a number of mediators.

The mediators that are immediately released include histamine, tryptase, chymase, kinins, and heparin. The mast cells quickly synthesize other mediators, including leukotrienes and prostaglandin D2. These mediators, via various interactions, ultimately lead to the symptoms of rhinorrhea (ie, nasal congestion, sneezing, itching, redness, tearing, swelling, ear pressure, postnasal drip). Mucous glands are stimulated, leading to increased secretions. Vascular permeability is increased, leading to plasma exudation. Vasodilation occurs, leading to congestion and pressure. Sensory nerves are stimulated, leading to sneezing and itching. All of these events can occur in minutes; hence, this reaction is called the early, or immediate, phase of the reaction.

Over 4-8 hours, these mediators, through a complex interplay of events, lead to the recruitment of other inflammatory cells to the mucosa, such as neutrophils, eosinophils, lymphocytes, and macrophages. This results in continued inflammation, termed the late-phase response. The symptoms of the late-phase response are similar to those of the early phase, but less sneezing and itching and more congestion and mucus production tend to occur. The late phase may persist for hours or days. Systemic effects, including fatigue, sleepiness, and malaise, can occur from the inflammatory response. These symptoms often contribute to impaired quality of life.

Chronic urticaria, defined as urticaria that persists for longer than 6 weeks, is a frustrating condition for both patients and caregivers. Urticaria is not a single disease but a reaction pattern that represents cutaneous mast cell degranulation, resulting in extravasation of plasma into the dermis. Urticaria is characterized by hives or wheals, which are edematous pruritic papules or plaques. The variety of potential triggers of urticaria, especially for acute urticaria, can make the approach to diagnosis and treatment a challenge. Patients with chronic urticaria may not improve or may depend on medication for years to relieve symptoms.

The primary subgroups of chronic urticaria include physical urticaria (ie, symptomatic dermatographism, cholinergic urticaria, pressure urticaria), urticaria secondary to an underlying medical condition, and chronic idiopathic urticaria. Physical urticaria, which is reproducible with the appropriate stimuli, can be identified with a thorough history and challenge testing.

Traditionally, the approach in patients with chronic urticaria (when physical etiology has been excluded) has been to order a panel of laboratory tests to uncover an occult medical condition responsible for the skin findings. In many patients, an extensive workup does not uncover an etiology. Urticaria rarely is the sole manifestation of an underlying medical problem. Patients in whom no explanation for the urticaria is established are said to have chronic idiopathic urticaria; however, findings suggest that in 25-45% of patients, chronic idiopathic urticaria is not idiopathic but is an autoimmune disease termed chronic autoimmune urticaria.

An important entity in the differential diagnosis of chronic urticaria is urticarial vasculitis. A forme fruste of leukocytoclastic vasculitis, urticarial vasculitis may be associated with hypocomplementemia and systemic symptoms.

The mast cell is the primary agent in the pathogenesis of urticaria. Mast cell stimulation results in the release of both preformed (histamine) and newly formed (prostaglandins) mediators from cytoplasmic granules, which cause wheal formation, vasodilatation, and erythema. Mast cells also release chemoattractants for other cells (eg, neutrophils) that also are involved in wheal formation. A number of mediators may be involved in the pathogenesis of urticaria, which may explain why antihistamines are not always effective therapy.

After eliminating the physical urticarias and urticarial vasculitis, chronic urticaria can be divided into autoimmune chronic urticaria (45%) and idiopathic chronic urticaria (55%).[2] Immunoglobulin G autoantibodies to the alpha subunit of the Fc receptor of the immunoglobulin E (IgE) molecule (35-40%) or, less commonly, anti-IgE autoantibodies (5-10%), can activate basophils to release histamine. This response may be augmented by complement activation and production of C5a. Unlike pulmonary mast cells, cutaneous mast cells have C5a receptors. C5a not only brings about mast cell activation, but is also a neutrophil and eosinophil chemoattractant, leading to accumulation of these cells in lesional skin.

Dermal mast cells secrete preformed mediators, including histamine (mainly the cause of pruritus.), proteases, interleukin 1, and tumor necrosis factor-alpha. The cytokines cause increased expression of adhesion molecules by endothelium of postcapillary venules.

Approximately one third of patients with chronic urticaria have either or both antithyroglobulin antibody and antimicrosomal antibody, and up to one fifth have abnormal thyroid function. A positive functional anti-FcεR test result supports an autoimmune basis. A positive test result does not indicate which autoantibody (anti-IgE, anti-FcεRI, or anti-FcεRII) is present. Affected patients may be categorized as having autoimmune chronic urticaria.

Mast cells may be degranulated through an IgE- and IgG-independent mechanism in chronic urticaria. Other non-IgE-mediated mast cell degranulators include radiocontrast media, morphine, codeine, and vancomycin. Approximately one third of patients with chronic urticaria may develop angioedema after administration of aspirin or other nonsteroidal anti-inflammatory drugs.

Approximately 85% of histamine receptors in the skin are of the H1 subtype, with the remaining 15% being H2 receptors. The addition of an H2 receptor antagonist to an H1 receptor antagonist augments the inhibition of a histamine-induced wheal-and-flare reaction once histamine-receptor blockade has been maximized. The combination of H2 receptor antagonists with an H1 receptor antagonist provides small additional benefit. Doxepin blocks both types of histamine receptors and is a much more potent inhibitor of H1 receptors than diphenhydramine or hydroxyzine.

Sinusitis is characterized by inflammation of the lining of the paranasal sinuses. Because the nasal mucosa is simultaneously involved and because sinusitis rarely occurs without concurrent rhinitis, rhinosinusitis is now the preferred term for this condition.

Rhinosinusitis may be further classified according to the anatomic site (maxillary, ethmoidal, frontal, sphenoidal), pathogenic organism (viral, bacterial, fungal), presence of complication (orbital, intracranial), and associated factors (nasal polyposis, immunosuppression, anatomic variants).

Acute sinusitis is a clinical diagnosis; thus, an understanding of its presentation is of paramount importance in differentiating this entity from allergic or vasomotor rhinitis and common upper respiratory infections. No specific clinical symptom or sign is sensitive or specific for acute sinusitis, so the overall clinical impression should be used to guide management.

The primary goals of management of acute sinusitis are to eradicate the infection, decrease the severity and duration of symptoms, and prevent complications. Most patients with acute sinusitis are treated in the primary care setting. Further evaluation by an otolaryngologist is recommended in any of the following cases: When continued deterioration occurs with appropriate antibiotic therapy; When episodes of sinusitis recur; When symptoms persist after 2 courses of antibiotic therapy When comorbid immunodeficiency, nosocomial infection, or complications of sinusitis are present Many classifications, both clinical and radiological, have been proposed in the literature to define acute sinusitis. Subacute sinusitis represents a temporal progression of symptoms for 4-12 weeks. Recurrent acute sinusitis is diagnosed when 2-4 episodes of infection occur per year with at least 8 weeks between episodes and, as in acute sinusitis, the sinus mucosa completely normalizes between attacks. Chronic sinusitis is the persistence of insidious symptomatology beyond 12 weeks, with or without acute exacerbations.

Chronic sinusitis is one of the more prevalent chronic illnesses in the United States, affecting persons of all age groups. It is an inflammatory process that involves the paranasal sinuses and persists for 12 weeks or longer. The literature has supported that chronic sinusitis is almost always accompanied by concurrent nasal airway inflammation and is often preceded by rhinitis symptoms; thus, the term chronic rhinosinusitis (CRS) has evolved to more accurately describe this condition. Most cases of chronic sinusitis are continuations of unresolved acute sinusitis; however, chronic sinusitis usually manifests differently from acute sinusitis. Symptoms of chronic sinusitis include nasal stuffiness, postnasal drip, facial fullness, and malaise. Chronic sinusitis may be noninfectious and related to allergy, cystic fibrosis, gastroesophageal reflux, or exposure to environmental pollutants. Allergic rhinitis, nonallergic rhinitis, anatomic obstruction in the ostiomeatal complex, and immunologic disorders are known risk factors for chronic sinusitis.

Medical therapy is directed toward controlling predisposing factors, treating concomitant infections, reducing edema of sinus tissues, and facilitating the drainage of sinus secretions. The goal in surgical treatment is to reestablish sinus ventilation and to correct mucosal opposition in order to restore the mucociliary clearance system. Surgery strives to restore the functional integrity of the inflamed mucosal lining.

Adult rhinosinusitis has certain diagnostic criteria. Major factors included facial pain or pressure, nasal obstruction or blockage, nasal discharge or purulence or discolored postnasal discharge, hyposmia or anosmia, purulence in nasal cavity, and fever; including confirmatory radiographic or nasal endoscopic or physical examination findings in addition to suggestive history.

Inflammation often is characterized by a strong infiltration of polymorphonuclear leukocytes at the site of inflammation, particularly neutrophils. These cells promote tissue damage by releasing toxic substances at the vascular wall or in uninjured tissue. Neutrophil infiltration results from amplifying cascades of cell-cell communication involving signal transduction proteins, such as G-proteins, that can facilitate intracellular regulation and intercellular communication by interacting with a wide range of different regulatory receptor-transducer proteins, such as membrane bound receptors.

As used herein, "joint" is meant to include the more or less movable junction in the body where two or more bones meet and the different kinds of ligaments, tendons, cartilages, bursae, synovial membranes and bones comprising the mobile skeletal-system of a mammal in various quantities and configurations. The composition of the present invention is useful with joints including, but not limited to, ankles, hips, shoulders, knees, wrists, fingers, toes and the like.

In some embodiments, the composition of the present invention has:
   at least one stimulant and at least one anti-histamine composition or a pharmaceutically acceptable salt thereof;
   a carrier, and
   optionally, an additional active ingredient.

In some embodiments, the composition of the present invention can be administered either orally, cutaneously, nasally, parenterally, vaginally, rectally, or bucally.

As used herein, "oral" or "orally" refers to introduction into the body by mouth whereby absorption occurs in one or more of the following areas of the body: the mouth, stomach, small intestine, lungs (also specifically referred to as, inhalation), and the small blood vessels under the tongue (also specifically referred to as, sublingually) (e.g., as liquid, syrup, lozenge, drops, films, gum, candy, sublingual tab or film, and the like, as known in the art). "Nasal" or "nasally," as used herein, refers to introduction into the body through the nose whereby absorption occurs through the thin mucous membrane that lines the nasal passages. In some embodiments, the composition of the present invention is in the form of a dispersible dry powder for delivery by inhalation or insufflation (either orally or nasally). Dry powder compositions may be prepared by processes known in the art, such as lyophilization and jet milling, as disclosed in International Patent Publication No. WO 91/16038 and U.S. Pat. No. 6,921,527, the disclosures of which are incorporated by reference. In some embodiments, the composition of the present invention for nasal or oral inhalation or insufflation administration is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol, and then capturing the aerosol produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522; U.S. Pat. No. 4,192,309; and U.S. Pat. No. 4,105,027. Suitable containers also include those used in conjunction with GlaxoSmithKline's Ventolin® Rotohaler brand powder inhaler (Research Triangle Park, N.C., USA) or sanofi-aventis's Spinhaler® brand powder inhaler (Holmes Chapel, UK, formerly, Fisons Plc., Loughborough, UK). Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with GlaxoSmithKline's diskhaler, e.g., Ventolin Disks® (U.S. Pat. Nos. 4,627,432; 4,811,731; and 5,035,237).

As used herein, "cutaneous" or "cutaneously" refers to application to the skin for a local (topical) effect or bodywide (systemic) effect such as that achieved percutaneously (transdermally). Cutaneous administration involves "topical administration" or "topically applying," which describes the direct application onto one or more surfaces including epithelial surfaces covering an affected area, e.g., a joint. Such a composition can be applied by, e.g., pouring, dropping, spraying, or wiping or rubbing on if a liquid; rubbing or wiping on, if an ointment, lotion, cream, paste, gel, or the like; dusting, if a powder; spraying, if an aerosol composition; or by any other appropriate means. When the composition is sprayed it can be from a compressed air source or pump. Cutaneous administration also can involve the use of transdermal administration such as transdermal patches or iontophoresis devices, which are prepared according to techniques and procedures well known in the art. The terms "transdermal delivery system", transdermal patch" or "patch" refer to an adhesive system placed on the skin to deliver a time-released dose of a drug(s) by passage from the dosage form through the skin to be available for distribution via the systemic circulation. Transdermal patches are a well-accepted technology used to deliver a wide variety of pharmaceuticals, including, but not limited to, scopolaminee for motion sickness, nitroglycerin for treatment of angina pectoris, clonidine for hypertension, estradiol for post-menopausal indications, and nicotine for smoking cessation. Patches suitable for use in the present invention include, but are not limited to, (1) the matrix patch; (2) the reservoir patch; (3) the multi-laminate drug-in-adhesive patch; (4) the monolithic drug-in-adhesive patch; and (5) bandage. (See e.g., *Transdermal And Topical Drug Delivery Systems*, pp. 249-297 (Tapash K. Ghosh et al. eds., 1997.)) These patches are well known in the art and generally available commercially. In some embodiments, the composition of the present invention for treating symptoms associated with inflammation or promoting healthy joints is administered by a route that is cutaneous.

As used herein, "parenteral" or "parenterally" refers to introduction into the body by way of an injection (i.e., administration by injection), including, for example, subcutaneously (i.e., an injection beneath the skin), intramuscularly (i.e., an injection into a muscle), intravenously (i.e., an injection into a vein), and intrathecally (i.e., an injection into the space around the spinal cord). A parenterally administered composition of the present invention is delivered using a needle, e.g., a surgical needle. "Surgical needle," as used herein, refers to any needle adapted for delivery of fluid compositions (i.e., capable of flow) of the present invention into a selected anatomical structure. In some embodiments, the composition of the present invention for treating symptoms associated with inflammation or promoting healthy joints is administered by a route that is parenteral.

"Vaginal" or "vaginally," as used herein, refers to introduction into the body through the vagina where absorption occurs through the vaginal wall. In some embodiments, the composition of the present invention for treating symptoms associated with inflammation or promoting healthy joints is administered by a route that is vaginal.

"Rectal" or "rectally," as used herein, refers introduction into the body through the rectum where absorption occurs through the walls of the rectum. The compositions of the present invention for rectal administration can be in the form of suppositories. These compositions can be prepared by mixing the drug with a suitable nonirritating excipient such as cocoa butter and polyethylene glycols, which are solid at ordinary temperatures but liquid at the rectal temperature, and will, therefore, melt in the rectum and release the drug. When formulated as a suppository the compositions of the invention may be formulated with traditional binders and carriers, such as triglycerides. In some embodiments, the composition of the present invention for treating symptoms associated with inflammation or promoting healthy joints is administered by a route that is rectal.

"Buccal" or "buccally," as used here in, refers to introduction into the body by, adjacent to, or toward the cheek such as in the area between the teeth and mucous membranes of the cheek. In some embodiments, the composition of the present invention for treating symptoms associated with inflammation or promoting healthy joints is administered by a route that is buccal.

In some embodiments of the present invention, the composition further has at least one penetration enhancer or propellant. A "penetration enhancer," as used herein, is an agent known to accelerate the delivery of a substance through the skin by, e.g., disrupting the barrier function of the skin without compromising its barrier effects on microorganisms and toxins. The penetration enhancer used in the invention should be applicable to skin (e.g., human) and compatible with the compound. Suitable penetration enhancers for this invention include, for example, and without limitation, such substances as dipolar-aprotic solvents, which include dimethylsulfoxide ("DMSO"), dimethyl formamide ("DMF"), N,N-dimethylacetamide ("DMA"), decylmethylsulfoxide ("$C_{10}$MSO"), and N-methyl-2-pyrrolidone, the 1-substituted azacycloheptane-2-ones, particularly 1-n-dodecylcyclazacycloheptan-2-one (available under the trademark Azone® from Whitby Research Incorporated, Richmond, Va.), phospholipids such as lecithin, alcohols including glycerols such as polyethylene glycol monolaurate ("PGML"), glycerol monolaurate ("GML"), and fatty acid alcohols, allantoin, urazole, and the like. The penetration enhancer also can be a vegetable oil, such as, but not limited to, safflower oil, cottonseed oil, corn oil, olive oil. Additional penetration enhancers generally can be found in *Remington: The Science and Practice of Pharmacy*, 20$^{th}$ ed. (Gennaro, A. R., et al., eds.) Lippincott Williams & Wilkins: Philadelphia (2000), which is incorporated herein by reference. As used herein, "propellant" refers to an agent that propels the delivery of a composition in, e.g., a vaporized, aerosol nebulized, or spray form. Propellants often are used in metered-dose inhalers for the treatment of asthma and other respiratory disorders and for systemic treatments such as insulin for diabetes. Propellants also are used, for example, in nasal inhalers for treatment of allergic rhinitis, topical sprays, oral sprays, and other aerosol applications. An example of such propellants, without limitation, are the Dymel® pharmaceutical propellants manufactured by DuPont™ (Wilmington, Del.).

In some embodiments, the composition of the present invention includes a pharmaceutically acceptable penetration enhancer. The term "pharmaceutically acceptable penetration enhancer," as used herein, refers to any substantially non-toxic substance that improves the bioavailability of the composition of the present invention. Pharmaceutically acceptable penetration enhancers are useful conventionally for topical administration of pharmaceuticals in which, e.g., the stimulant and anti-histamine compound remains stable and bioavailable when applied directly to skin.

As used herein, the terms "carrier" and "pharmaceutical carrier" refer to a pharmaceutically acceptable inert agent or vehicle for delivering one or more active agents to a mammal, and often is referred to as "excipient." The (pharmaceutical) carrier must be of sufficiently high purity and of sufficiently low toxicity to render it suitable for administration to the mammal being treated. The (pharmaceutical) carrier further should maintain the stability and bioavailability of an active agent, e.g., a stimulant and anti-histamine compound of the present invention. The (pharmaceutical) carrier can be liquid or solid and is selected, with the planned manner of administration in mind, to provide for the desired bulk, consistency, etc., when combined with an active agent and other components of a given composition. The (pharmaceutical) carrier can be, without limitation, a binding agent (e.g., pregelatinised maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulphate, etc.). Other suitable (pharmaceutical) carriers for the compositions of the present invention include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like. Compositions of the present invention that are for cutaneous administration of the stimulant and anti-histamine compound, such as topical (i.e., local), can include (pharmaceutical) carriers such as sterile and non-sterile aqueous solutions, non-aqueous solutions in common solvents such as alcohols, or solutions of the stimulant and anti-histamine compound in liquid or solid oil bases. Such (pharmaceutical) carrier solutions also can contain buffers, diluents and other suitable additives. Compositions of the present invention that are for parenteral administration of the stimulant and anti-histamine compound, such as intramuscular or subcutaneously, can include (pharmaceutical) carriers such as sterile aqueous solutions, non-aqueous solutions in common solvents such as alcohols, or solutions of the stimulant and anti-histamine compound in a liquid oil base.

In some embodiments, the carrier of the composition of the present invention includes a release agent such as sustained release or delayed release carrier. In such embodiments, the carrier can be any material capable of sustained or delayed release of the stimulant and anti-histamine compound to provide a more efficient administration, e.g., resulting in less frequent and/or decreased dosage of the stimulant and anti-histamine compound, improve ease of handling, and extend or delay effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

As used herein, "moisturizing agent" refers to a substance that adds or restores moisture to the skin or a mucous membrane. Representative examples of moisturizing agents (often referred to as humectants) that are suitable in the present invention include, but are not limited to, guanidine, glycolic acid and glycolate salts, Aloe vera in any of its variety of forms, allantoin, urazole, polyhydroxy alcohols such as sorbitol, glycerol, hexanetriol, polypropylene glycol, butylene glycol, hexylene glycol and the like, polyethylene glycols, sugars and starches and their derivatives, hyaluronic acid, lactamide monoethnolamine, acetamide mono ethanol amine, and any combination thereof.

As used herein, "fragrance," refers to a substance having a pleasant aroma Suitable fragrances include, without limitation, eucalyptus oil, camphor synthetic, peppermint oil, clove oil, lavender, chamomile, and the like.

The term "chelating agent," as used herein, refers to a ligand, atom, ion or functional group that binds to a metal ion such as calcium ($Ca^{2+}$), magnesium ($Mg^{2+}$) and copper ($Cu^{2+}$, forming a metal complex known as a chelate. In some embodiments of the present invention, the composition further optionally contains a chelating agent, e.g., a mild agent, such as, ethylenediaminetetraacetic acid ("EDTA"), EDTA derivatives, or any combination thereof. In some embodiments, the chelating agent enhances the preservative or preservative system of the composition. Suitable preservatives for use in the compositions of the present invention include, but are not limited to, one or more alkanols, disodium EDTA, EDTA salts, EDTA fatty acid conjugates, isothiszolinone, parabens such as methylparaben and propylparaben, polypropylene glycols, sorbates, urea derivatives such as diazolindinyl urea, or any combination thereof.

The term "emulsifiers," as used herein, promote the formation and stabilization of an emulsion. Suitable emulsifiers can be natural materials, finely divided solids, or synthetic materials. Natural emulsifying agents can be derived from either animal or vegetable sources. Those from animal sources include, e.g., gelatin, egg yolk, casein, wool fat, and cholesterol. Those from vegetable sources include, e.g., acacia, tragacanth, chondrus, and pectin. Vegetable sources specifically from cellulose derivatives include, e.g., methyl cellulose and carboxymethyl cellulose, and often are used to increase viscosity. Finely divided emulsifiers include, e.g., bentonite, magnesium hydroxide, aluminum hydroxide, and magnesium trisilicate. Synthetic emulsifiers include, e.g., anionic, cationic, or nonionic agents such as sodium lauryl sulfate, benzalkonium chloride, polyethylene glycol 400 monostearate and any combinations thereof.

The term "thickeners," as used herein, refers to agents that make a composition dense or viscous in its consistency. Suitable thickeners for the compositions of the present invention include, e.g., non-ionic water-soluble polymers such as hydroxyethylcellulose (commercially available under the trademark Natrosol® 250 or 350), cationic water soluble polymers such as Polyquat 37 (commercially available under the trademark Synthalen®CN), fatty alcohols, fatty acids, anionic polymers and their alkali salts, and mixtures thereof.

As used herein, "solublizing agents" refers to substances that enable a solute to dissolve in a medium in which the solute is otherwise insoluble. Representative examples of solublizing agents that are suitable in the present invention include, without limitation, complex-forming solublizers such as citric acid, EDTA, sodium meta-phosphatate, succinic acid, urea, cyclodextrin, polyvinylpyrrolidone, diethylammonium-ortho-benzoate, and micelle forming solubilizers such as TWEEN® polysorbates (e.g. TWEEN 80® and TWEEN 60®) and Span sorbitan esters (e.g. sorbitan monostearate (Span 60) and sorbitan monoleate (Span 80)). Other solublizers that are useful in the compositions of the present invention are, for example, polyoxyethylene sorbitan fatty acid esters, polyoxyethylene n-alkyl amine n-oxides, polyoxamers, organic solvents such as acetone, phospholipids, and cyclodextrins.

As used herein, "anti-irritant" refers to an agent that prevents or reduces soreness, roughness, or inflammation of a body part. Suitable anti-irritants for use in the present invention include, for example, steroidal and non-steroidal anti-inflammatory agents or other materials such as Aloe vera, chamomile, alpha-bisabolol, cola nitida extract, green tea extract, tea tree oil, licoricic acid, allantoin, caffeine or other xanthines, glycyrrhizic acid and its derivatives, and mixtures thereof. Anti-irritants can be divided into water-soluble anti-irritants and water-insoluble anti-irritants with representative examples described in, for example U.S. Pat. No. 5,482,710, which is incorporated herein by reference.

The term "colorant," as used herein, refers to a substance that gives or changes color of a composition, and includes pigments or dyes or a combination thereof. Suitable pigments for use in the compositions of the present invention include, without limitation, iron oxides and titanium oxides, while suitable dyes include FD&C approved colorants, D&C approved colorants, and those approved for use in Europe and Japan. See Marmion, D. N., "Handbook of U.S. Colorants for Food, Drugs, Cosmetics, and Medical Devices," $3^{rd}$ ed., 1991 (John Wiley & Sons, New York), incorporated herein by reference.

The term "surfactants," as used herein, refers to surface-active substances, such as a detergent. Suitable surfactants for use with the present invention include, but are not limited to, sarcosinates, glutamates, sodium alkyl sulfates, ammonium alkyl sulfates, ammonium alkyleth sulfates, ammonium laureth-n-sulfates, sodium laureth-n-sulfates, isothionates, glycerylether sulfonates, sulfosuccinates and combinations thereof. In some embodiments, the composition of the present invention includes an anionic surfactant selected from the group consisting of sodium lauroyl sarcosinate, monosodium lauroyl glutamate, sodium alkyl sulfates, ammonium alkyl sulfates, sodium alkyleth sulfates, and combinations thereof.

In some embodiments, the composition of the present invention treats or prevents inflammation or symptoms associated or related to inflammation. In some embodiments, the inflammation is associated with a joint condition, inflammation of the airways, or inflammatory bowel disease. In some embodiments, the joint condition includes arthritis or a joint injury. The joint injury can be a sprain, ligament tear, tendon tear, strained ligament, strained tendon, ligament rupture, tendon rupture, cartilage tear, or some other joint injury.

In some embodiments, the inflammation of the airways being treated or prevented by a composition of the present invention includes an asthma or chronic obstructive pulmonary disease. In some embodiments, the asthma is chronic. In some embodiments, the chronic obstructive pulmonary disease includes chronic bronchitis and emphysema; or chronic bronchitis. In some embodiments, the inflammatory bowel disease includes ulcerative colitis and Crohn's disease; ulcerative colitis; or Crohn's disease.

The term "disease" or "disorder," as used herein, refers to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. A "joint injury," as used herein, includes a variety of conditions resulting from some mechanical damage to a joint due to some outside force being applied to the joint, or due to turning, extending, flexing, twisting, or otherwise using the joint in a way that does damage to its component tissues and/or compromises its ability to function normally. The term "condition," as used herein, refers to a variety of health states and is meant to include disorders or diseases, injury, the promotion of healthy joints, tissue and organs, and inflammation caused by any underlying mechanism or disorder.

In some embodiments, the composition of the present invention is a pharmaceutical composition. A "pharmaceutical composition," as used herein, refers to a composition, which has under gone federal regulatory review, that prevents, reduces in intensity, cures, ameliorates, or otherwise treats a target disorder or disease.

In some embodiments, the stimulant and anti-histamine compound of the composition of the present invention is contained within a botanical extract. Botanical extracts can be assayed for stimulant and anti-histamineactivity by using the methods described herein. As used herein, a "botanical extract" refers to a fresh or processed (e.g., cleaned, frozen, dried, sliced, liquefied) part of a single species of plant, alga or macroscopic fungus.

In some embodiments, the stimulant and anti-histamine compound of the composition of the present invention is contained within a microbial extract. As used herein, "microbial extract" refers to a fresh or processed (e.g., cleaned, frozen, dried, liquefied, dissolved, pelleted) part of a microbial culture. The term "microbial," "microbe" or "microorganism," as used herein, refers to an organism too small to be seen clearly with the naked eye, including, but not limited to, bacteria, fungi, molds, algae, protozoan and viruses. Microbial extracts can be assayed for stimulant and anti-histamine activity according to the methods described herein.

In some embodiments, the composition of the present invention has an additional active ingredient. As used herein, "additional active ingredient" refers to an agent, other than a stimulant and anti-histamine compound of the present invention, that exerts a pharmacological, dermatological or any other beneficial activity. The additional active ingredient should be compatible with the stimulant and anti-histamine compound of the present invention. The term "compatible," as used herein, means that the active ingredients of a composition are capable of being combined with each other in a manner such that there is no interaction that would substantially reduce the efficacy of each active ingredient or the composition under ordinary use conditions. It is to be understood that "other beneficial activity" can be one that is perceived only as such by the subject using the inventive compositions. In some embodiments, the stimulant and anti-histamine compound of the inventive composition is a new excipient. As used herein, a "new excipient" refers to any inactive ingredient that is added intentionally to the composition of the present invention and is not intended to exert a therapeutic effect at the intended dosage, although it may act to improve product delivery. A new excipient is not fully qualified by existing safety data with respect to the currently proposed level of exposure, duration of exposure, or route of administration. Additional characteristics of new excipients can be found in the "Guidance for Industry Nonclinical Studies for the Safety Evaluation of Pharmaceutical Excipients" issued by the Center for Drug Evaluation and Research, U.S. Food and Drug Administration, in May 2005, herein incorporated by reference.

In some embodiments, the compositions of the present invention further can include one or more compatible active ingredients that are aimed at providing the composition with another pharmaceutical effect, in addition to that provided by a stimulant and anti-histamine compound of the inventive composition.

In some such embodiments, the additional active ingredient is selected from one or more protective agent, demulcent, emollient, astringent, steroidal anti-inflammatory agent, non-steroidal anti-inflammatory agent, antioxidant, chemotherapeutic agent, antihistamine agent, cleansing agent or combination thereof.

Non-limiting examples of additional active ingredients that can be used in addition to at least one stimulant and at least one anti-histamine for treating inflammation related effects can include one or more of the following.

Numerous materials have been used to treat chronic or uncontrolled inflammation, all of which suffer from side effects, some of which are serious, if not life-threatening. For example, products used for relief of inflammation include, without limitation, corticosteroids and NSAIDs (Non-Steroid Anti-Inflammatory Drugs). Corticosteroids, a class of steroids, are used clinically to suppress or control inflammation. The sub-class of corticosteroids known as glucocorticoids are anti-inflammatory by, amongst other mechanisms, preventing phospholipid release and decreasing eosinophil action. Representative examples of corticosteroids useful in reducing inflammation include, without limitation, betamethasone, budesonide, cortisone, dexamethasone, hydrocortisone, methylprednisolone, prednisolone, predinsone, triamcinolone, corticosteroid preparations containing salicylic acid derivatives, and other corticosteroidal topical products for joint and muscular pain that also include tolazoline and dimethyl sulfoxide ("DMSO"). Common side effects of corticosteroids include increased appetite and weight gain, deposits of fat in chest, face, upper back and stomach, water and salt retention leading to swelling and edema, high blood pressure, diabetes, excess sweating, telangiectasia (dilation of capillaries), slowed healing of wounds, osteoporosis, cataracts, acne, hirsutism, muscle weakness, atrophy of the skin and mucous membranes, an increased susceptibility to infection, and stomach ulcers.

As the name suggests, NSAIDs are not steroids, though these compounds have a similar eicosanoid-depressing action to steroids in achieving their anti-inflammatory effect. Representative examples of NSAIDs include, without limitation, aspirin, mofebutazone, clofezone, oxyphenbutazone, benzydamine, etofenamate, piroxicam, felbinac, bufexamac, ketoprofen, bendazac, naproxen, ibuprofen, fentiazac, diclofenac, feprazone, niflumic acid, meclofenamic acid, flurbiprofen, tolmetin, suxibuzone, indomethacin, and nifenazone. Aspirin or salicyclic acid is the first discovered member of the NSAIDs class. NSAIDs are not all salicylates, but they have similar effects and mechanisms of action. NSAIDS generally block the activity of the cyclooxygenase (COX) genes, with some blocking both the COX-1 and COX-2 genes, while others more selectively block only one of the two genes. For example, aspirin blocks both COX genes, while the newer celecoxib (Celebrex®, Pfizer, Inc., New York, N.Y.), rofecoxib (Vioxx®, Ceoxx® and Ceeoxx®, Merck & Co., Whitehouse Station, N.J.), and valdecoxib (Bextra®, Pfizer) act specifically on the COX-2 gene, and consequently, are often referred to as COX-2 selective inhibitors or coxibs (CycloOXygenase-2 inhiBitors). Other coxibs include, e.g., Etoricoxib (Arcoxia®, Pfizer) and lumiracoxib (Prexige®, Novartis, Basel, Switzerland).

The specificity of coxibs allows these NSAIDs to reduce inflammation with minimal gastrointestinal side effects, such as dyspepsia, ulcer perforation, and upper gastrointestinal bleeding that are common with NSAIDs that act on both COX genes. Studies, however, have demonstrated an increased risk of cardiovascular events associated with the use of the coxibs celecoxib, valdecoxib and parecoxib than with other NSAIDs. Side-effects of NSAIDS vary between drugs, but generally include nausea, vomiting, diarrhea, constipation, decreased appetite, rash, dizziness, headache, drowsiness and photosensitivity. NSAIDs also may cause fluid retention, leading to edema. The most serious side effects of NSAIDs use are kidney failure, liver failure, ulcers and prolonged bleeding after an injury or surgery. NSAIDs can produce shortness of breath in individuals allergic to them. People with asthma are at a higher risk for experiencing serious allergic reaction to NSAIDs. Individuals with a serious allergy to one NSAID are likely to experience a similar reaction to a different NSAID.

In the broadest pharmacological sense a "protective agent" or "protectives," as used herein, refers to any agent that isolates the exposed surface of skin or membrane (e.g., mucous membrane) from harmful or annoying stimuli. A protective can take the form of dusting powders, adsorbents, mechanical protective agents, and plasters. Dusting powders are relatively inert and insoluble materials that are used to cover and protect, e.g., epithelial surfaces, ulcers, and wounds. Usually these substances are finely subdivided powders that absorb moisture and can act as a desiccant. The absorption of skin moisture decreases friction and also discourages certain bacterial growth. Some of the materials that are used as protective adsorbents include bentonite, insoluble salts of bismuth, boric acid, calcium carbonate (precipitated), cellulose, corn starch, magnesium stearate, talc, titanium dioxide, zinc oxide, and zinc stearate.

A protective also can be administered to the skin to form an adherent, continuous film that can be flexible or semi-rigid depending on the materials and the formulations as well as the manner in which they apply. This protective material can serve several purposes including providing occlusion from the external environment, providing chemical support, and serving as vehicles for other medicaments. Mechanical protectives generally are either collodions or plasters. Examples include, without limitation, aluminum hydroxide gel, collodions, dimethicone, petrolatum gauze, adsorbable gelatin film, adsorbable gelatin sponge, zinc gelatin, kaolin, lanolin, anhydrous lanolin, mineral oil, mineral oil emulsion, mineral oil light, olive oil, peanut oil, petrolatum, silicones, and the like.

Demulcents are protective agents that are employed primarily to alleviate irritation, particularly mucous membranes or abraded tissues. They often are applied to the surface in viscid, sticky preparations that cover the area readily and can be medicated. A number of chemical substances possess demulcent properties. These substances include, e.g., the alginates, mucilages, gums, dextrins, starches, certain sugars, and polymeric polyhydric glycols. Other demulcents include, e.g., acacia, agar, benzoin, carbomer, gelatin, glycerin, hydroxyethyl cellulose, hydroxypropyl cellulose, hydroxypropyl methylcellulose, propylene glycol, sodium alginate, tragacanth, and the like.

The term "emollients," as used herein refers to substances that generally are bland, fatty, or oleaginous materials that can be applied locally, particularly to skin. Emollients are moisturizers that increase the tissue moisture content thereby rendering the skin softer and more pliable. Increased moisture content in the skin can be achieved by preventing water loss with an occlusive water-immiscible barrier, increasing the water-holding capacity in the skin with humectants or altering the desquamation of the outermost skin layer, the stratum corneum. Useful emollients for the present invention include, e.g., lanolin, spermaceti, mineral oil, paraffin, petrolatum, white ointment, or yellow ointment, and the like; as well as, e.g, vegetable oils, waxes, cetyl alcohol, glycerin, hydrophilic petrolatum, isopropyl myristate, myristyl alcohol, and oleyl alcohol.

The term "astringents," as used herein, refers to compounds that are applied locally to tissue (e.g., skin) such as protein precipitants that have such low cell penetrability that the action is limited essentially to the cell surface and interstitial spaces. The astringent action is accompanied by contraction and wrinkling of the tissue and by blanching. Astringents are used therapeutically to arrest hemorrhage by coagulating the blood, promote healing, toughen the skin, or decrease sweating. The principle components of astringents are salts of aluminum, zinc, manganese, iron, or bismuth. Certain other salts may also be used, such as permanganates and tannins, or related polyphenolic compounds and the like.

The term "cleansing agents," as used herein, includes detergents (i.e., soaps) and non-soap detergents, and the like.

The term "irritant," as used herein, refers to a material that acts locally on the skin to induce, based on irritant concentration, hyperemia, inflammation, and vesication. The agents that induce only hyperemia are also known as rubefacients. A "rubifacient," as used herein, refers to a material that produces increased circulation to an injured area, accompanied by a feeling of comfort, warmth, and sometimes itching and hyperesthesia. Some of these standard irritants are alcohol, aromatic ammonia spirits, benzoin tincture, camphor capsicum, coal tar extracts and the like.

The term "steroidal anti-inflammatory agent," as used herein, refers to any one of numerous compounds containing a 17-carbon 4-ring system including, e.g., the sterols, various hormones (such as anabolic steroids), and glycosides. Representative examples of steroidal anti-inflammatory agents include, without limitation, corticosteroids such as hydrocortisone, hydrooxyltriamcinolone, alpha-methyl dexamethasone, dexamethasone-phosphate, beclomethasone dipropionates, clobetasol valerate, desonide, deoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprenylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its estes, chloroprednisone, chloroprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

The term "non-steroidal anti-inflammatory agent" or "NSAID," as used herein, refers to a large group of agents, as previously described herein. Examples of non-steroidal anti-inflammatory agents that are suitable for the compositions of the present invention include, without limitation, aspirin, ibuprofen, naproxen sodium, oxicams, such as piroxicam, isoxicam, tenoxicam, sudoxicam, and CP-14,304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acemetacin, fentiazac, zomepirac, clindanac, oxepiniac, felbinac, and ketorolac; fenamates, such as mefenamic, meclofenamic, flufenamic, niflumic, and tolfenamic acids; propionic acid derivatives, such as ibuprofen, naproxen, benoxaprofen, fluribiprofen, ketoprofen, fenoprofen, fenbufen, indopropfen, pirprofen, caipofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, trimethazone. Mixtures of non-steroidal anti-inflammatory agents also can be employed, as well as the pharmaceutically and/or dermatologically-acceptable salts and esters thereof such as etofenamate, a flufenamic acid derivative, which is particularly useful for topical administration.

The term "antioxidant agent," as used herein, refers to a substance that inhibits oxidation or reactions promoted by oxygen or peroxides. Non-limiting examples of antioxidants that are suitable for the compositions of the present invention include, e.g., ascorbic acid (vitamin C) and its salts, ascorbyl esters of fatty acids, ascorbic acid derivatives (e.g., magnesium ascorbyl phosphate, sodium ascorbyl phosphate, and ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine and amino-guanidine), sulfhydryl compounds (e.g., glutathione), dihydroxy fumaric acid and it salts, glycine pidolate, arginine pilolate, nordihydroguaiaretic acid, bioflavinoids, curcumin, lyseine, methionine, proline, superoxide dismutase, silymarin, tea extracts, grape skin and seed extracts, melanin, and rosemary extracts.

The term "chemotherapeutic agent," as used herein, refers to a chemical useful in the treatment or control of a disease. Non-limiting examples of chemotherapeutic agents suitable for the present invention include daunorubicin, doxorubicin, idarubicin, amrubicin, pirarubicin, epirubicin, mitoxantrone, etoposide, teniposide, vinblastine, mitomycin C, fluorouracil (5-FI), paclitaxel, docetaxel, actinomycin D, colchicines, topotecan, irinotecan, geincitabine cyclosporine, verapamil, valspodor, probenecid, (E)-3-[[[3-[2-(7-chloro-2-quinolinyl) ethenyl]phenyl]-[[3-dim ethylamino)-3-oxopropyl]thio]methyl]thio]-propanoic acid (MK571), N-(4[2-(1,2,3,4-tetrahydro-6,7-dimethoxy-2-isoquinolyl)-ethyl]-phenyl-9,10-dihydro-5-methoxy-9-oxo-4-acridine carboxamide (elacridar, GF129918), zosuquidar trihydrochloride (LY335979), biricodar, terfenadine, quinidine, pervilleine A and tariquidar (XR9576).

The term "antihistamine agent," as used herein, refers to a compound that counteracts histamine in the body and is used for treating allergic reactions and cold symptoms. Non-limiting examples of antihistamine agents suitable for the present invention include chlorpheniramine, brompheniramine, dexchloropeniramine, tripolidine, clemastine, diphenhydramine, promethazine, piperazines, piperidines, astemizole, loratadine, levocetirizine dihydrochloride, 4-(4-(bis(4-fluorophenyl)methyl)piperazin-1-ylbut-2-enyloxy)acetic acid (SUN-1334H), cetirizine, fexofenadine, and terfenadine.

The term "hormone," as used herein, refers to a natural substance produced by organs of the body that travel by blood to trigger activity in other locations or their synthetic analogs. Suitable hormones for the present invention include, but are not limited to, calciferol (Vitamin $D_3$) and its products, androgens, estrogens, and progesterones.

The term "caustic agent," as used herein, refers to substances capable of destroying or eating away epithelial tissue by chemical action. Caustic agents can be used to remove dead skin cells. For example, beta-hydroxy acids, which are naturally derived acids with a strong kerolytic effect, are useful for acne or peeling outer layers of the skin.

In some embodiments, the composition of the present invention includes a mixture selected from a solution, emulsion, suspension and powder. In some such embodiments, the suspension is a gel, aerosol or paste. As used herein, "suspension" refers to a colloidal mixture in which a finely-divided species is combined with another species, with the former being so finely divided and mixed that it does not rapidly settle out A suspension of liquid droplets or fine solid particles in a gas is called an "aerosol." As used herein, "paste" refers to a suspension that behaves as a solid until sufficient stress is applied, at which point it flows like a fluid. As used herein, "gel" refers to a suspension having a dispersed phase with a dispersion medium or matrix, resulting in a viscous, jelly-like, semisolid material. When water is the dispersion medium the gel is often referred to as a hydrogel.

In some such embodiments, the composition is a solution. A solution is generally considered as a homogeneous mixture of two or more substances; it is frequently, though not necessarily, a liquid. In a solution, the molecules of the solute or dissolved substance are uniformly distributed among those of the solvent. Solvents that can be useful in the compositions of the present invention include water, as well as organic solvents such as the alcohols (e.g. ethanol or isopropanol, acetone).

In some embodiments, the composition of the present invention is an emulsion. As used herein, "emulsion" refers to a colloid system in which both the dispersed phase and the dispersion medium are immiscible liquids where the dispersed liquid is distributed in small globules throughout the body of the dispersion medium liquid. The globule size is critical and must be such that the system achieves maximum stability. Usually, separation of the two phases will occur unless a third substance, an emulsifying agent, is incorporated. Thus, a stable basic emulsion contains at least the two liquids and the emulsifying agent, and often additionally, an active agent. Common types of emulsions are oil-in-water, where oil is the dispersed liquid and an aqueous solution, such as water, is the dispersion medium, and water-in-oil, where conversely, an aqueous solution is the dispersed phase. It is possible also to prepare emulsions that are basically non-aqueous, for example, using anionic and cationic surfactants of the non-aqueous immiscible system of glycerol and olive oil. An emulsion of a composition of the present invention can have a number of other materials that are immiscible along with the compound of the present invention (e.g., AFC). When the composition of this invention is an emulsion including AFC, non-lipid based vehicles are preferred due to the lipophilic nature of the compound. Emulsifying agent carriers useful in the present invention are described hereinabove.

In some embodiments, the compositions of the present invention can be mixed with a gel suspension (a semisolid carrier) or solid carrier to form a paste, powder, ointment, cream, lotion, hydrogel, and the like. In some such embodiments, the compositional form is an ointment. An ointment is a semi-solid preparation often intended for external application to the skin. Generally, ointment bases are categorized into hydrocarbon bases (oleaginous), which may use white petrolatum as a base; adsorption bases (anhydrous), which might use hydrophilic petrolatum or anhydrous lanolin; emulsion bases (water and oil type); and water soluble bases, which often use polyethylene glycol as an ointment base.

Additional compositions of the present invention can be prepared using technology readily known in the art such as described in *Remington: The Science and Practice of Pharmacy*, $20^{th}$ ed. (Gennaro, A. R., et al., eds.) Lippincott Williams & Wilkins: Philadelphia (2000).

In some embodiments, the composition includes the stimulant and anti-histamine compound in an amount that is from about 0.01% to about 50%, expressed on a % w/w compositional basis. In some embodiments, the amount of stimulant and anti-histamine compound in the composition is from about 0.1% to about 20%, expressed on a % w/w compositional basis. In some embodiments, the amount of stimulant and anti-histamine compound in the composition is no more than about 10%, expressed on a % w/w compositional basis. In some embodiments, the amount of stimulant and anti-histamine compound in the composition is from about 0.01% to about 5%, expressed on a % w/w compositional basis.

Another aspect of the present invention, is related to a method of treating symptoms associated with inflammation in a mammal in need thereof or for promoting healthy joints, the methods comprising administering to the mammal a pharmaceutically effective amount of a composition of the present invention.

As used herein the terms "pharmaceutically effective amount," refers to any amount of a composition of the present invention that results in a therapeutic or beneficial effect following its administration to a subject. The pharmaceutical effect can be curing, minimizing, preventing, or ameliorating a condition, syndrome, injury, disease or disorder, improving the physical appearance and aesthetics, or the effect can any other pharmaceutical beneficial effect. The concentration of the substance is selected so as to exert its pharmaceutical effect, but low enough to avoid significant side-effects within the scope and sound judgment of the skilled artisan. The effective amount of the composition can vary with the particular condition, syndrome, injury, disease or disorder being treated, prevented or promoted (e.g., healthy joints), the age and physical condition of the mammal to whom the composition is being administered, the severity of the condition, injury, syndrome disease or condition, the duration of the administration, the nature of concurrent therapy, the specific compound of the present invention, composition or other active ingredient employed, the particular carrier utilized, and like factors.

A skilled artisan can determine a pharmaceutically effective amount of the inventive compositions by determining the unit dose. As used herein, "unit dose" refers to the amount of inventive composition required to produce a response of 50% of maximal effect (i.e., $ED_{50}$). The unit dose can be assessed by extrapolating from dose-response curves derived from in vitro or animal model test systems. Non-limiting examples include the use of:

Caffeine: 5-1000 mg of caffeine, e.g., 5, 10, 15, 20, 25, 30, 35, 40, 50, 60, 70, 80, 90, 100, 110, 120, 130, 140, 150, 175, 200, 225, 250, 275, 300, 325, 350, 375, 400, 425, 475, 500, 525, 550, 575, 600, 625, 650, 675, 700, 750, 800, 850, 900, 950, 1000 mg, or any range or value therein, e.g., but not limited to 20-500 mg, 50-100, 50-200, 100-500, and the like, per dose, which can be given every 1-12 hours, 1-12 times a day, 1-7 days a week, or 1-30 days per week or any range or value therein, e.g., but not limited to, every 4-12 hours, e.g., 2, 3, 4, 5, 6, 7, 8, 9, 10, 11 or 12 hours.

Cetirizine: 0.1-100 mg of cetirizine, e.g., 0.5, 1.0, 1.5, 2.0, 2.5, 3.0, 3.5, 4.0, 5.0, 6.0, 7.0, 8.0, 9.0, 10.0, 11.0, 12.0, 13.0, 14.0, 15.0, 17.5, 20.0, 22.5, 25.0, 27.5, 30.0, 32.5, 35.0, 37.5, 40.0, 42.5, 47.5, 50.0, 52.5, 55.0, 57.5, 60.0, 62.5, 65.0, 67.5, 70.0, 75.0, 80.0, 85.0, 90.0, 95.0, 100.0 mg, or any range or value therein, e.g., but not limited to 0.20-50.0 mg, 50-10.0, 5.0-20.0, 10.0-50.0, and the like, per dose, which can be given every 1-12 hours, 1-12 times a day, 1-7 days a week, or 1-30 days per week or any range or value therein, e.g., but not limited to, every 4-12 hours, e.g., 2, 3, 4, 5, 6, 7, 8, 9, 10, 11 or 12 hours.

Fexofenadine: 0.1-500 mg of fexofenadine, e.g., 0.5, 1.0, 1.5, 2.0, 2.5, 3.0, 3.5, 4.0, 5.0, 6.0, 7.0, 8.0, 9.0, 10.0, 11.0, 12.0, 13.0, 14.0, 15.0, 17.5, 20.0, 22.5, 25.0, 27.5, 30.0, 32.5, 35.0, 37.5, 40.0, 42.5, 47.5, 50.0, 52.5, 55.0, 57.5, 60.0, 62.5, 65.0, 67.5, 70.0, 75.0, 80.0, 85.0, 90.0, 95.0, 100.0, 110, 120, 130, 140, 150, 160, 170, 180, 190, 200, 210, 220, 230, 240, 250, 275, 300, 350, 400, 450, 500 mg, or any range or value therein, e.g., but not limited to 0.20-50.0 mg, 0.50-10.0, 5.0-20.0, 10.0-50.0, and the like, per dose, which can be given every 1-12 hours, 1-12 times a day, 1-7 days a week, or 1-30 days per week or any range or value therein, e.g., but not limited to, every 4-12 hours, e.g., 2, 3, 4, 5, 6, 7, 8, 9, 10, 11 or 12 hours.

Loratadine: 0.1-100 mg of loratadine, e.g., 0.5, 1.0, 1.5, 2.0, 2.5, 3.0, 3.5, 4.0, 5.0, 6.0, 7.0, 8.0, 9.0, 10.0, 11.0, 12.0, 13.0, 14.0, 15.0, 17.5, 20.0, 22.5, 25.0, 27.5, 30.0, 32.5, 35.0, 37.5, 40.0, 42.5, 47.5, 50.0, 52.5, 55.0, 57.5, 60.0, 62.5, 65.0, 67.5, 70.0, 75.0, 80.0, 85.0, 90.0, 95.0, 100.0 mg, or any range or value therein, e.g., but not limited to 0.20-50.0 mg, 50-10.0, 5.0-20.0, 10.0-50.0, and the like, per dose, which can be given every 1-12 hours, 1-12 times a day, 1-7 days a week, or 1-30 days per week or any range or value therein, e.g., but not limited to, every 4-12 hours, e.g., 2, 3, 4, 5, 6, 7, 8, 9, 10, 11 or 12 hours.

Levocetirizine dihydrochloride: 0.1-100 mg of levocetirizine dihydrochloride, e.g., 0.5, 1.0, 1.5, 2.0, 2.5, 3.0, 3.5, 4.0, 5.0, 6.0, 7.0, 8.0, 9.0, 10.0, 11.0, 12.0, 13.0, 14.0, 15.0, 17.5, 20.0, 22.5, 25.0, 27.5, 30.0, 32.5, 35.0, 37.5, 40.0, 42.5, 47.5, 50.0, 52.5, 55.0, 57.5, 60.0, 62.5, 65.0, 67.5, 70.0, 75.0, 80.0, 85.0, 90.0, 95.0, 100.0 mg, or any range or value therein, e.g., but not limited to 0.20-50.0 mg, 0.50-10.0, 5.0-20.0, 10.0-50.0, and the like, per dose, which can be given every 1-12 hours, 1-12 times a day, 1-7 days a week, or 1-30 days per week or any range or value therein, e.g., but not limited to, every 4-12 hours, e.g., 2, 3, 4, 5, 6, 7, 8, 9, 10, 11 or 12 hours.

4-(4-(bis(4-fluorophenyl)methyl)piperazin-1-ylbut-2-enyloxy)acetic acid (SUN-1334H): 0.1-100 mg of 4-(4-(bis(4-fluorophenyl)methyl)piperazin-1-ylbut-2-enyloxy)acetic acid, e.g., 0.5, 1.0, 1.5, 2.0, 2.5, 3.0, 3.5, 4.0, 5.0, 6.0, 7.0, 8.0, 9.0, 10.0, 11.0, 12.0, 13.0, 14.0, 15.0, 17.5, 20.0, 22.5, 25.0, 27.5, 30.0, 32.5, 35.0, 37.5, 40.0, 42.5, 47.5, 50.0, 52.5, 55.0, 57.5, 60.0, 62.5, 65.0, 67.5, 70.0, 75.0, 80.0, 85.0, 90.0, 95.0, 100.0 mg, or any range or value therein, e.g., but not limited to 0.20-50.0 mg, 50-10.0, 5.0-20.0, 10.0-50.0, and the like, per dose, which can be given every 1-12 hours, 1-12 times a day, 1-7 days a week, or 1-30 days per week or any range or value therein, e.g., but not limited to, every 4-12 hours, e.g., 2, 3, 4, 5, 6, 7, 8, 9, 10, 11 or 12 hours.

In some embodiments, the method of the present invention treats or prevents inflammation resulting from a disease, condition, syndrome, injury or disorder of an anatomical system selected from the group consisting of a cardiovascular system, a cerebrovascular system, a digestive system, an integumentary system, a muscular system, a nervous system, a reproductive system, a respiratory system, a skeletal system, an endocrine system and a urinary system.

In some embodiments, the method of the present invention treats or prevents inflammation resulting from a joint condition, inflammation of the airways or inflammatory bowel disease. In some embodiments, the joint condition includes an arthritis or a joint injury. In some embodiments, the joint condition includes arthritis. In some embodiments, the joint condition includes joint injury. In some embodiments, the method for treating or preventing a joint condition involves administering the composition of the present as previously described herein.

In some embodiments, the method of the present invention treats or prevents inflammation resulting from inflammation of the airways. In some embodiments, the inflammation of the airways includes asthma or chronic pulmonary obstructive disease; asthma; or chronic obstructive pulmonary disease. In some embodiments, the method for treating symptoms associated with inflammation of the airways involves administering the composition of the present invention as previously described herein.

In some embodiments, the method of the present invention treats or prevents the inflammation resulting from inflammatory bowel disease. In some such embodiments, the inflammatory bowel disease includes ulcerative colitis and Crohn's disease; ulcerative colitis; or Crohn's disease. In some embodiments, the method for treating or preventing inflammatory bowel disease involves administering the composition of the present invention as previously described herein.

In some embodiments, the method of the present invention promotes healthy joints. In some embodiments, the method involves administering the composition of the present invention as previously described herein.

In another aspect of the present invention, two or more stimulant and anti-histamine compounds are used in the inventive composition to obtain a specific pharmaceutical or cosmeticeutical effect.

Without being bound by any particular theory, in some embodiments of the present invention, the stimulant and antihistamine compound acts by prevent post-translational carboxyl methylation; in some embodiments, the stimulant and anti-histamine compound acts by inhibiting polyisoprenyl cysteine methyltransferase.

In another aspect, the present invention relates to a kit providing components for administering a composition of the present invention. In some embodiments, the kit of the present invention has a composition of the present invention for parenteral administration, as previously described herein, and a needle. In some embodiments, the kit has a plurality of individual dosage units containing a parenteral composition of the present invention, and a plurality of needles, thereby providing a quantity of the composition for administration during a regimen. In some embodiments, the regimen includes daily, a week, two weeks, three weeks, a month (e.g., about 28 to about 31 days). In some embodiments, administration of the composition of the present invention involves an extended regimen, which comprises a plurality of kits of the present invention so as to allow an extended period of administration. An extended regimen can be a plurality of months, a year, a plurality of years, or a period until the inflammation decreases or ceases. In some embodiments, the regimen is lifelong (i.e., continuing through life).

The present invention described herein has both human and veterinarian utility, and can be administered to animals of the ayes, reptilia, or mammalia classes. In some embodiments of the methods of the present invention, the composition is administered to animals selected from birds, reptiles or mammals. In some embodiments of the methods of the present invention, the animal is a mammal. In some embodiments, the mammal is human. In some embodiments, the mammal is nonhuman.

A further aspect of the present invention relates to a method for preparing the previously described compositions of the present invention. In some embodiments, the method for preparing the composition of the present invention includes the step of admixing at least one stimulant and anti-histamineor pharmaceutically acceptable salt thereof, a carrier and optionally, an additional active ingredient.

In preparing cutaneously-administered compositions of the present invention, (e.g., topical skin application), in order to avoid irritation, the compositions can be prepared having a pH value between about 4.0 and about 7.0, preferably between about 5.0 and about 7.0, most preferably about 6.0 or substantially 6.5. In some embodiments, the method of preparing a cutaneously-administered composition of the invention further includes adjusting the composition by adding a pH adjusting agent until the desired pH value is achieved. In some embodiments, the method for preparing the composition of the present invention further includes the step of adjusting the pH of the composition to a pH value from about 4.0 to about 7.0; from about 5.0 to about 7.0; from about 6.0 to about 6.5; or substantially 6.5. Suitable pH adjusting agents include, for example, but are not limited to, one or more adipic acids, glycines, citric acids, calcium hydroxides, magnesium aluminometasilicates, buffers, or any combination thereof. In some embodiments, the method of preparing the compositions of the present invention further includes adding at least one penetration enhancer or propellant. The mixing technique utilized in the method of preparing the composition of the present invention can involve any one of the known techniques for formulating compositions. A variety of exemplary formulation techniques that are usable in the process of the present invention is described, for example, in *Harry's Cosmeticology*, 7th edition, Edited by J. B. Wilkinson, and R. J. Moore, Longman Scientific & Technical, 1982, which is incorporated herein by reference.

While the compositions discussed herein do not necessarily treat the underlying disease state that may give rise to the inflammatory diseases and disorders, the compositions of the present invention can be useful for diminishing or alleviating the inflammation. In some embodiments, the composition of the present invention treats or prevents the underlying condition, injury, syndrome, disease or disorder as well as inflammation. In some embodiments, the composition treats or prevents substantially inflammation, i.e., it does not also treat or prevent the underlying condition, injury, syndrome, disorder or disease.

When a range of values is provided, it is understood that each intervening value, to the tenth of the unit of the lower limit unless context clearly dictates otherwise, between the upper and lower limit of that range and any other stated or intervening value in that stated range is encompassed within the present invention. The upper and lower limits of these smaller ranges, which may be included independently in the smaller ranges, also is encompassed within the present invention, subject to any specifically excluded limit in the stated range. When the stated range includes one or both of the limits, ranges excluding either or both of those included limits are included also in the present invention.

Unless defined otherwise, all technical and scientific terms used herein have the same meaning as commonly understood by one of ordinary skill in the art to which this invention belongs. Although any methods and materials similar or equivalent to those described herein also can be used in the practice or testing of the present invention, the preferred methods and materials are now described. AU publications mentioned herein are incorporated herein by reference to disclose and describe the methods and/or materials in connection with which the publications are cited.

It must be noted that as used herein and in the appended claims, the singular forms "a", "and", and "the" include plural references including at least one or one or more, unless the context clearly dictates otherwise.

EXAMPLES OF MODELS

The following are examples of models in which to test the efficacy of stimulant and anti-histamine compounds as a new class of inflammation acting compounds that can mimic, e.g., but not limited to, the effectiveness of corticosteroids in inflammation processes without the undesirable side effects of corticosteroids. Such examples are not intended to limit the scope of what the inventors regard as their invention nor have the inventors intended to represent that the in models below are the only ones that should or could be used to test the efficacy of the present invention.

Topical Inflammation Models

Example 1

Stimulant and Anti-Histamine Compound, e.g., Caffeine in Combination With One or More of Loratadine, Fexofenadine, or Cetirizine (C/L, F, or C), in an Acetone Carrier Suppresses TPA-Elicited Edema in the Murine Ear Acute Contact Irritation Model In order to assess the effects of a representative composition of the present invention, a composition of (C/L, F, or C) for reducing edema in the mouse ear model, an established model of dermal inflammation, is used. (See Carlson, R. P., et al., *Modulation of mouse ear edema by cyclooxygenase and lipoxygenase inhibitors and other pharmacologic agents*. Agents Actions, 1985. 17(2): 197-204; Kuehl, F. A., Jr., et al., *Role of prostaglandin endoperoxide PGG 2 in inflammatory processes. Nature*, 1977. 265(5590): 170-3; Trancik R J, L. N., *Evaluation of topical nonsteroidal anti-inflammatory agents, in Models in Dermatology*, L. Maibach, Editor. 1985, Karger. pp. 35-42; and Tramposch, K. M., *Skin Inflammation, in In Vivo Models of Inflammation*, M. L. Morgan D W, Editor. 1999, Birkhauser Verlag. pp. 179-204.)

Examples of standard agents for initiating inflammation are the phorbol ester, tetradecanoylphorbol acetate, (TPA) and arachidonic acid (AA). TPA produces a greater and more prolonged neutrophil infiltration response than AA (See Rao, T. S., et al., *Comparative evaluation of arachidonic acid (AA)-and tetradecanoylphorbol acetate (TPA)-induced dermal inflammation*. Inflammation, 1993.17(6): 72341.) TPA-induced inflammation is the preferred agent and is used for this example.

Dose Response Curve for Irritant.

A dose response range for TPA, a compound known to induce edema, is determined TPA produces an increase in edema (ear swelling) that reaches a maximum at 6 hours.

Increasing concentrations of TPA dissolved in acetone are applied with the aid of a micropipetter onto the right ear of each of the five 6-8 week old, male Swiss Webster mice used in this analysis. Ten microliters (10 μl) are spread evenly onto the inner and outer surfaces using the pipette tip. The mice then are returned to their cages. The contralateral ear is treated only with acetone. After 5.5 hours, the mice are sacrificed and 6 mm punches are taken from each ear and weighed. Edema response is expressed as a percent increase in the treated ear's weight over the untreated ear. The dose response curve, as well as an $ED_{50}$ value, is determined using the Lichtfield method (Lichtfield J T W. F., *A simplified method of evaluating dose-effect experiments*, Journal of Pharmacology and Experimental Therapeutics, 1948, 96: 99-113).

The increase in ear weight depends on TPA dose from 0.25 to 1.75 μg/20 μl, reaching a maximum increase of approximately 150% of the acetone-treated ear. Doses between 1.5-2.0 μg/20 μl can be suitable to use in eliciting edema in future tests of anti-inflammatory agents.

Stimulant and Anti-Histamine Compound (C/L, F, or C) in an Acetone Carrier, Itself, is Not an Irritant.

A range of from about: [REVISE:] 5 mg to about 32 mg (C/L, F, or C), is mixed with 20 μl acetone to produce an inventive (C/L, F, or C) composition. Each concentration is applied with the aid of a micropipetter onto the right ear of each of six mice so that 10 μl of each of the concentrations of the (C/L, F, or C) inventive compositions are applied to an inner ear surface and 10 μl is applied to an outer ear surface of the right ear. The (C/L, F, or C) inventive compositions are spread evenly with a pipette tip. Each contralateral ear is treated with only acetone in the same manner. The mice then are returned to their cages. After 5.5 hours, mice are sacrificed and 6 mm punches are taken from each ear and weighed. Edema response is expressed as the percent increase in the treated ear's weight over the untreated (acetone, vehicle only) ear.

(C/L, F, or C) in acetone alone are expected to have no effect on the edema response. The (C/L, F, or C) inventive compositions had no effect on the ear punch biopsy weight at a dose up to about [REVISE:] 32 mg/20 μl. (C/L, F, or C) did not induce edema on its own at doses 60-fold greater than doses having efficacy against chemically-induced edema. This finding suggests an excellent safety profile for (C/L, F, or C).

Result of (C/L, F, or C) Inventive Composition on TPA-Induced Edema.

In order to assess the effects of the inventive composition on TPA-induced edema, 2 μg of TPA in 20 μl acetone is applied with the aid of a micropipetter onto both ears of each of 6 mice. The mice are returned to their cages. Fifteen minutes later, increasing concentrations of (C/L, F, or C) in 10 μl of acetone are applied to the inside and outside surfaces of the right ears as described above. Twenty microliters (20 μl) of an acetone vehicle is applied similarly to the left ear of each mouse as an internal negative control. After treatment, the mice are returned to their cages for 5.5 hours. The mice are sacrificed by cervical dislocation. The ears are immediately removed at their base and a 6 mm diameter punch biopsy is taken from the center of each ear. The ear punch is weighed on an analytical balance for edema measurements as described above. The ability of the various concentrations of (C/L, F, or C) to inhibit TPA-induced edema is assessed by determining the difference in weight between the (C/L, F, or C)-treated ear and the acetone (vehicle)-only treated ear over the increase in ear punch weight induced by TPA.

When (C/L, F, or C) is tested in this acute inflammation mouse-ear assay, (C/L, F, or C) and is expected to reduce acute chemically induced inflammation significantly as compared to the use of C, L, F or C alone or additively. The inventive composition is expected to reduce the TPA-induced ear weight increase in a dose dependent manner. The inventive composition is expected to result in 25-80% reduction in edema. The $ED_{50}$ of the inventive (C/L, F, or C) composition is expected to be 2-20 times that of the use of stimulant or antihistamine alone or additively for TPA-induced edema inhibition.

The results are expected to show that the combination of caffeine combined with loratadine, cetirizine or fexofenadine have synergistic and/or unexpected reduction or improvement of inflammation and associated symptoms as compared to the use of caffeine or loratadine or cetirizine or fexofenadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Example 2

AFC Inhibits TPA-Induced Neutrophil Infiltration in Mice

TPA Induces Neutrophil Infiltration in Mice.

Acute contact irritants such as TPA can also induce dermal infiltration of neutrophils. This may or may not be independent of the reduction of edema, as: 1) the maximum neutrophil response is delayed relative the maximal edema response; 2) some irritants will induce edema independent of neutrophil infiltration; and 3) some of the known anti-inflammatory agents reduce one, but not the other. (See Rao, T. S., et al., *Comparative evaluation of arachidonic acid (AA)-and tetradecanoylphorbol acetate (TPA)-induced dermal inflammation*. Inflammation, 1993, 17(6): 723-41.) In this experiment, the aim is to determine if topically applied (C/L, F, or C) would affect neutrophil infiltration in response to acute topical irritation produced by TPA.

Neutrophil-infiltration Assay: Swiss Webster male mice (n=6) are treated with 1 μg/20 μl of TPA as described above in order to assess whether or not TPA induced neutrophil infiltration Acetone is used as a control. TPA is administered as described above. The mice are returned to their cages for 24 hrs to allow neutrophil infiltration, then sacrificed by cervical dislocation. The ears are removed immediately for punch biopsy, and punches are fixed for subsequent histological analysis and MPO enzymatic assay.

MPO Assay: This assay measures myeloperoxidase, ("MPO") which is packaged in the primary granules of mature granulocytes including the neutrophil. Thus, the amount of MPO in the ear is proportional to the number of infiltrating neutrophils.

MPO enzyme activity of the ears is assayed using the technique detailed by Griffiths and coworkers (1988). To conduct the assay, each ear is homogenized in 1.0 ml of cetyltrimethylammonium bromide buffer for 5 sec using a Pro 200 tissue blender (Pro Scientific, Inc., Oxford, Conn.) at setting 5. These samples then are centrifuged for 5 minutes at 15,000 rpm in a 5415 Eppendorf microcentrifuge. Triplicate 20 microliter aliquots of supernatant are added to 200 microliters of reaction mixture (1.25 ml 1M Potassium Phosphate, 4.175 mg o-dianisidine dihydrochloride and 5 µl of 1% peroxide in a final volume of 25 ml). Absorbance at 450 nm then is measured at room temperature at three 60 second intervals using Bio-Kinetics Reader EL 312E (Bio-Tek Instruments). Activity of the homogenate, which is determined by a Bradford assay (BioRad Protein Assay, BioRad Laboratories, Inc. Hercules, Calif.), is expressed as units MPO per mg tissue+/− standard error.

Neutrophil Counting Assay: Ear punches buffered in 10% formalin in PBS at ambient temperature for a minimum of 24 hrs. are sectioned and stained with Hematoxilin & Eosin ("H & E"). The number of neutrophils, identified by their multilobular nuclei, in 6 randomly 100× magnified fields distributed along the length of the ear are counted manually The results are expressed as the average number per field for each ear.

(C/L, F, or C) Inhibits TPA-Induced Neutrophil Infiltration.

Inventive (C/L, F, or C) compositions also are used to assess efficacy in the reduction of dermal neutrophil infiltration. (See Rao, T. S., et al., *Comparative evaluation of arachidonic acid (AA)-and tetradecanoylphorbol acetate (TPA)-induced dermal inflammation*. Inflammation, 1993. 17(6): 723-4 for a discussion regarding the relationship between edema and neutrophil infiltration and the effect of known anti-inflammatory agents on these variables.)

Two micrograms (2 µg) of TPA in 20 µl of acetone is applied onto both ears of each mouse to induce neutrophil infiltration. After 15 minutes, varying concentrations of (C/L, F, or C) in acetone are applied to the right ear of each mouse. After 24 hours, the mice are sacrificed. The ears are removed and the efficacy of (C/L, F, or C) on neutrophil infiltration is assessed by an MPO assay and histological analysis.

MPO Analysis

The results are expected to show that (C/L, F, or C) acts to reduce neutrophil infiltration in a dose dependent manner when neutrophil infiltration is measured by an MPO analysis, as compared to C, L, F, or C alone or additively. When (C/L, F, or C) is tested in the Neutrophil-Infiltration Assay, it is expected to have little or no inflammation activity of its own. The data are expected to indicate that (C/L, F, or C) produces at least 50-80% inhibition of TPA-induced increases in MPO activity and an suitable $ED_{50}$.

Neutrophil Counts:

This histological analysis is expected to demonstrate efficacy of (C/L, F, or C) in suppressing dermal neutrophil infiltration in response to acute contact irritation. The presence of neutrophils in the TPA alone treated ears is observed clearly at 24 hours after treatment. Essentially no neutrophils are observed in the ears that are not exposed to TPA. In the ears pretreated with TPA and then treated with vehicle or (C/L, F, or C), the numbers of neutrophils are expected to be comparable between vehicle plus TPA-treated ear and ears treated with TPA alone. A substantial reduction of neutrophils is expected to be observed in the (C/L, F, or C) treated ear.

Upon counting the neutrophils, suitable amounts of (C/L, F, or C) are expected to produce statistically significant and at least 50-80% reduction in dermal neutrophils produced in response to acute contact irritation by TPA. (Statistical significance is calculated using a Student's paired t-test).

The Effect of (C/L, F, or C) on Neutrophils is Time Dependent

The effectiveness of (C/L, F, or C) treatment at various times before and after TPA application is assessed using MPO as a measure of neutrophil infiltration. In this example, both ears of six mice are treated with a suitable dose of TPA in acetone. The right ear then is treated with a suitable dose of (C/L, F, or C) inventive composition at various times before and after TA application, while simultaneously treating the contralateral ear with acetone.

The results are expected to show the efficacy of (C/L, F, or C) treatment prior to, simultaneous with, or after exposure of skin to TPA. There is a gradual decrease in MPO activity with time at which (C/L, F, or C) is applied after TPA application, the steroid dexamethasone is expected to show a similar time dependence. Thus, it can be anticipated that (C/L, F, or C) will act like steroids in reducing established inflammatory conditions.

These results are expected to support a wide range of possible cosmetic and pharmaceutical applications for the combination of (C/L, F, or C).

The results are expected to show that the combination of caffeine combined with loratadine, cetirizine or fexofenadine has synergistic and/or unexpected reduction or improvement of inflammation and associated symptoms as compared to the use of caffeine or loratadine or cetirizine or fexofenadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Example 3

The (C/L, F, or C) Inventive Composition does not Exhibit Systemic Effects

The effect of (C/L, F, or C) on TPA induction of neutrophil MPO activity is compared with two other agents representing different classes of commonly used anti-inflammatories that inhibit inflammation by mechanisms different from (C/L, F, or C). These include dexamethasone, a steroid, and indomethasone, a non-steroid anti-inflammatory drug, which targets cycloxygenases. The action of (C/L, F, or C) in this model is, therefore, compared to that of dexamethasone and indomethasone. Each of these agents are tested using the same protocols used to test (C/L, F, or C).

When the concentration of dexamethasone and indomethasone is increased, the contralateral vehicle-treated ear shows increasing inhibition of MPO activity, reflective of inhibition of neutrophil infiltration. This is evidence that topically applied dexamethasome and indomethasone are entering the circulation and exerting a systemic effect with increasing effective local doses. With (C/L, F, or C), no effect is expected to be seen on the vehicle-treated ear. Topically applied (C/L, F, or C), even at its highest effective local doses is not expected to be entering the circulation and, therefore, has no systemic effect in the mouse model.

Example 4

Effect of an (C/L, F, or C) and Acetone Composition on Arachadonic Acid-Induced Edema and Arachadonic Acid-Induced Neutrophil Infiltration Arachadonic acid ("AA"), another standard agent that is used routinely as a contact irritant in the mouse ear model to assay the effectiveness of both steroidal and nonsteroidal anti-inflammatory agents, is the metabolic precursor for a number of lipoxygenase and cyclooxygenase products. Its mechanism of action and, thus, the signaling pathways it activates, differ from those activated by topically applied TPA. AA produces a more rapid edema than TPA that peaks at 1 hour after application. There is minimal histologically observable neutrophil infiltration in response to AA, but an increase in MPO can be detected. Experience has shown that effectiveness against cyclooxygenase activated inflammation in this model is less predictive of effectiveness against human inflammatory diseases than effectiveness against TPA activated inflammation.

The effect of the inventive compositions on arachidonic acid (AA) induced inflammation is assayed using the same protocols as above, but with the following modifications. AA is applied to both ears at 4 mg/40 µl acetone. The ears are harvested at 1 hour to measure edema, the maximum response time, and at 5 hours for inflammatory neutrophil infiltration as measured by an MPO assay.

The (C/L, F, or C) inventive composition, prepared as described above, is expected to be at least as effective in reducing granulocyte infiltration induced by AA than TPA.

The results are expected to show that the combination of caffeine combined with loratadine, cetirizine or fexofenadine have synergistic and/or unexpected reduction or improvement of inflammation and associated symptoms as compared to the use of caffeine or loratadine or cetirizine or fexofenadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Example 5

(C/L, F, or C) Inventive Composition Visibly Reduces TPA-Induced Erythema

For this example, both ears of a mouse are treated with a 1 µg/20 µl dose of TPA in acetone. After 1 hour, the right ear is treated with 1 mg/20 µl of inventive (C/L, F, or C) composition and the left ear is treated with acetone alone. The photo is taken 23 hours later using a Nikon D70 digital camera. An effect of the (C/L, F, or C) inventive composition on TPA-induced erythema is expected to be observed.

The results are expected to show that the combination of caffeine combined with loratadine, cetirizine or fexofenadine have synergistic and/or unexpected reduction or improvement of inflammation and associated symptoms as compared to the use of caffeine or loratadine or cetirizine or fexofenadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Example 6

(C/L, F, or C) Inventive Compositions Reduce Inflammation in Humans When Pre-Applied An irritant is applied to the middle of the upper back of a human subject using a 0.2 ml 20% SDS solution and a Hill-Top Chamber patch with Webril pad. (C/L, F, or C), at a suitable concentration in aqueous formulation, is pre-applied to patch areas 1 a and 1 b. Patches 1 a and 2 a are removed after 2 hours, while patches 1 b and 2 b are removed after 2 hours and 30 minutes. High levels of irritation are visible in patch sites 2 a and 2 b. Site 1 a showed normal skin while 1 b is expected to show a mild response. These results are expected to show that the inventive composition can reduce or prevent inflammation when human skin is exposed to an irritant.

The results are expected to show that the combination of caffeine combined with loratadine, cetirizine or fexofenadine have synergistic and/or unexpected reduction or improvement of inflammation and associated symptoms as compared to the use of caffeine or loratadine or cetirizine or fexofenadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Example 7

The Effect of (C/L, F, or C) on Chronic Irritation in Mice

The effectiveness of the inventive compositions against established chronic irritation can be assayed using a modification of the technique of Stanley P L et al., *Mouse skin inflammation induced by multiple topical application 12-O-tetradeconoyphorbol-13-acetate*. Skin Pharmacol. 1991, 4(4):262-71. Both ears of each mouse are treated with TPA in acetone, as above, in a series of 5 applications on the mornings of days 0, 2, 4, 7, and 9. The treated ear receives the inventive compositions containing (C/L, F, or C) and acetone, in series of three paired applications, such that it is applied 6 hours apart on days 7, 8 and 9. Punches of the ears then are taken the afternoon of the tenth day and prepared, as above, for the edema assay and the infiltration of neutrophils. Total granulocyte infiltration then is assayed by measuring MPO activity. Macrophage infiltration is determined immunocytologically using the MOMA-2 antibody. Hydrocortisone, which is known to reduce inflammatory edema granulation infiltration and microphage infiltration, can be used as a positive control. It is contemplated that the results likely will show that (C/L, F, or C) in acetone reduces chronic edema and neutrophil number in mice.

The results are expected to show that the combination of caffeine combined with loratadine, cetirizine or fexofenadine have synergistic and/or unexpected reduction or improvement of inflammation and associated symptoms as compared to the use of caffeine or loratadine or cetirizine or fexofenadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Example 8

The Effect of the (C/L, F, or C) Inventive Composition on Delayed-Type Hypersensitivity The mouse ear model, described above, can be modified to assay the effect of anti-inflammatory agents in an immune based inflammation model (See Tramposch, K. M., *Skin Inflammation*, in *In Vivo Models of Inflammation*, M. L. Morgan D W, Editor. 1999, Birkhauser Verlag. pp. 179-20 and Chapman, J. P., Z. Ruben, and G. M. Butchko, *Histology of and quantitative assays for oxazolone-induced allergic contact dermatitis in mice*. Am J Dermatopathol, 1986. 8(2): 130-8). In this model, a sensitizing dose of dinitrofluorobenzene (DNFB) 1-3% in acetone can be applied topically according to a modification of the method by Back et al. to the shaved bellies of mice to elicit an immune response. (See Back, O. and T. Egelrud, *Topical glucocorticoids and suppression of contact sensitivity. A mouse bioassay of anti-inflammatory effects*. Br J Dermatol, 1985. 112(5): 539-45 and Bailey, S. C., et al., *A novel contact hypersensitivity model for rank-ordering formulated corticosteroids*. Inflamm Res, 1995. 44 Suppl 2: S162-3.) Mice then are challenged on day 5 with 40 µl of 0.5-1% DNFB to each ear. The (C/L, F, or C) inventive compound is applied either 0.5 hour before or 15 min after the challenge to one ear and the vehicle is applied to the other ear. The ears are assayed for edema or neutrophil infiltration 5 hours later. Dexamethasone is used as a positive control. Five days later, the ears are challenged topically with a dose of DNFB insufficient to produce contact irritation. Simultaneously, cell infiltration studies are initiated. It is predicted that there initially will be more neutrophils than macrophages; but by 48-72 hours, macrophages will be the predominant population. Its contemplated that no inflammatory response will be seen, and the inventive (C/L, F, or C) composition is, therefore, effective in reducing both edema and neutrophil infiltration.

The results are expected to show that the combination of caffeine combined with loratadine, cetirizine or fexofenadine have synergistic and/or unexpected reduction or improvement of inflammation and associated symptoms as compared to the use of caffeine or loratadine or cetirizine or fexofenadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Joint Inflammation Models

These models are used to show that the compounds of the present invention can treat or prevent joint inflammation.

Example 9

Lewis Rat Adjuvant-Induced Arthritis Model

Male Lewis rats are immunized with the adjuvant at the base of the tail on Day 0. On Day 7, 14, or 21 (or shorter or longer, depending on the study's goals) the rats' rear paw volume can be measured macroscopically by blinded observers for edema. The paws can then be amputated and x-raved for bone/joint destruction via a grading system of 0-4 called the "radiological index." Such a model is employed in Yamashita, A. et al. (2002) *The Journal of Immunology* 168: 450-457; Zhao, H. et al. (2000) *J. Orthop. Sci.* 5:397; and Barbier, A., et al. (1986) *Ann. Rheum. Dis.* 45:67.

The results are expected to show that the combination of caffeine combined with loratadine, cetirizine or fexofenadine have synergistic and/or unexpected reduction or improvement of inflammation and associated symptoms as compared to the use of caffeine or loratadine or cetirizine or fexofenadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Example 10

Type II Collagen Induced Arthritis

Male DBA-1/BOM mice are immunized in the tail with bovine type II collagen that has been prepared and emulsified with an adjuvant. After an incubation period, the paws of the mice are inspected macroscopically for edema and assigned a grade by independent, blinded observers. The whole joints can be removed, fixed, embedded in paraffin, sectioned, and stained for inflammatory cell infiltration. Bone and joint destruction, a characteristic of collagen-induced arthritis, can be measured as well. The collagen induced arthritis model using DBA-1/BOM mice is described by Lubberts, E. et al. (2000) *J. Clin. Invest.* 105: 1697; and Lubberts, E. et al. (2003) *J. Immunol.* 2003: 2655-2662.

The results are expected to show that the combination of caffeine combined with loratadine, cetirizine or fexofenadine have synergistic and/or unexpected reduction or improvement of inflammation and associated symptoms as compared to the use of caffeine or loratadine or cetirizine or fexofenadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Irritable Bowel Disease Model

This model can be used to show that the compounds of the present invention can treat or prevent inflammation caused by irritable bowel disease.

Example 11

Acetic Acid Induced Irritable Bowel Disease in Rats

Male Sprague-Dawley rats have IBS (irritable Bowel Syndrome) induced via intracolonic instillation of 4% acetic acid solution, and are allowed to recover for six days. On day seven, collection and measurement of inflammation is performed. Colonic segments are removed and put under tension to simulate motor activity of intestinal circular muscles. The effect of a drug on the colonic motor activity is quantified by measuring the mean intraluminal pressure at a given concentration. The mean intraluminal pressure is calculated digitally by dividing an integral value of pressure (area under the pressure trace) by the number of data points (tracing time). The acetic acid induced IBS model is described by La, J. H. et al. (2005) *World J. Gastroenterol.* 11(2): 237-241.

The results are expected to show that the combination of caffeine combined with loratadine, cetirizine or fexofenadine have synergistic and/or unexpected reduction or improvement of inflammation and associated symptoms as compared to the use of caffeine or loratadine or cetirizine or fexofenadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Induced Asthma Model

This model can be used to show that the compounds of the present invention treat or prevent inflammation of the airways.

Example 12

Rat Lung Sensitization with OVA and *Bordetella Pertussis*

INBRED Brown Norway rats are sensitized with ovalbumin (OVA) adsorbed in aluminum hydroxide dissolved in phosphate-buffered saline (PBS), and heat killed *Bordetella pertussis*. Then the rats undergo an airway challenge using 5% aerosolized OVA or bovine serum albumin (BSA) delivered through orotracheal intubation using a rodent pulmonary mechanics system. The lungs then are processed via 2 mM EDTA/PBS perfusion through the right ventricle; bronchoalveolar lavage (BAL) fluid samples are collected through tracheostomy, the lungs are fixed at 25 cm $H_2O$ by tracheobronchial infusion of 4% paraformaldehyde/PBS or 10% formalin BS; and tissue sections are obtained in parahilar and midsagittal orientation. This rat induced asthma model is described by Ramos-Barbón, D., et al. (2005) *J. Clin. Invest.* 115: 1580-1589.

The results are expected to show that the combination of caffeine combined with loratadine, cetirizine or fexofenadine have synergistic and/or unexpected reduction or improvement of inflammation and associated symptoms as compared to the use of caffeine or loratadine or cetirizine or fexofenadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Example 13

Caffeine/Loratadine Suppression of TNF-Alpha Production Via Activation of Cyclic AMP/Protein Kinase A Pathway Following the abstinence period from caffeine-containing food and beverages, heparinized venous blood is to be drawn from healthy volunteers. Blood is diluted to diluted 1:10 with RPMI 1640 tissue culture medium containing 1% (v/v) penicillin/streptomycin (Gibco Life Technologies, Scotland). Briefly, 400 ∝l aliquots of diluted whole blood are pipetted into wells of a sterile 48-well plate (Nunc, Denmark). To each well, 50 µl of either RPMI 1640 (control), loratadine (dissolved in RPMI 1640 to yield final concentrations between 1-10 µM loratadine), or loratadine/caffeine (dissolved in RPMI 1640 to yield final concentrations in culture of 10, 20, 50, and 100 µM caffeine and 1-10 µM loratadine). Following a 2 h incubation at 37° C. in a 5% CO2 atmosphere, 50 µl of lipopolysaccharide (LPS) from *Escherichia coli* (serotype 0111:B4) is added to each well at a final concentration of 1 µg/ml. Cultures are then be incubated for a further 24 h at 37° C. in a 5% CO2 atmosphere. At the end of the incubation period, culture supernatants are removed, centrifuged at 15,000×g for 15 min, and stored at −20° C. until the ELISAs are performed.

Measurement of Cytokines in Tissue Culture Supernatants

TNF-α, IL-1β, IL-12, and IL-10 is measured using commercially available enzyme-linked immunosorbent assays (Cytosets, Biosource International, USA). The assays are performed according to the manufacturer's instructions. Results are calculated as pg cytokine/ml of culture medium, and then expressed as percent control.

Measurement of Intracellular cAMP

Intracellular cAMP is measured in LPS-stimulated monocytes isolated from whole blood by adherence. Whole blood (100 µl) is added to wells of a 96-well tissue culture plate and incubated at 37° C., 5% CO2, for 1 h. After this time, wells are washed twice with 500 ∝l RPMI 1640 (heated to 37° C.). Complete RPMI 1640 [RPMI 1640+5% (v/v) heat-inactivated foetal calf serum+1% (v/v) penicillin/streptomycin] containing 10% (v/v) LPS (final concentration 1 µg/ml) is then added to the wells (100 ∝l/well) and incubated at 37° C., 5% CO2, for 23 h. After this time, 100 µl caffeine (final concentration 0-100 µM) is added to the wells, and cultures are incubated for a further 1 h. Intracellular cAMP is then measured using the Amersham cAMP EIA system, according to the manufacturer's instructions.

Statistical Analysis of Data

Data is analysed using a one- or two-way completely randomized analysis of variance. If any statistically significant change is found, post hoc comparisons are performed using either Dunnett's two-tailed test or Newman Keul's test where appropriate. Data is deemed significant when P<0.05. Data are expressed as group means with standard errors.

The results are expected to show that the combination of caffeine and loratadine have synergistic and/or unexpected reduction or improvement of inflammation and associated symptoms as compared to the use of caffeine or loratadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Example 14

Caffeine/Fexofenadine Suppression of TNF-Alpha Production Via Activation of Cyclic AMP/Protein Kinase a Pathway Following the abstinence period from caffeine-containing food and beverages, heparinized venous blood is to be drawn from healthy volunteers. Blood is diluted to diluted 1:10 with RPMI 1640 tissue culture medium containing 1% (v/v) penicillin/streptomycin (Gibco Life Technologies, Scotland). Briefly, 400 ∝l aliquots of diluted whole blood are pipetted into wells of a sterile 48-well plate (Nunc, Denmark). To each well, 50 µl of either RPMI 1640 (control), fexofenadine (dissolved in RPMI 1640 to yield final concentrations between 1-100 µM fexofenadine), or fexofenadine/caffeine (dissolved in RPMI 1640 to yield final concentrations in culture of 10, 20, 50, and 100 µM caffeine and 1-100 µM fexofenadine). Following a 2 h incubation at 37° C. in a 5% CO2 atmosphere, 50 µl of lipopolysaccharide (LPS) from *Escherichia coli* (serotype 0111:B4) is added to each well at a final concentration of 1 µg/ml. Cultures are then be incubated for a further 24 h at 37° C. in a 5% CO2 atmosphere. At the end of the incubation period, culture supernatants are removed, centrifuged at 15,000×g for 15 min, and stored at −20° C. until the ELISAs are performed.

Measurement of Cytokines in Tissue Culture Supernatants

TNF-α, IL-1β, IL-12, and IL-10 is measured using commercially available enzyme-linked immunosorbent assays (Cytosets, Biosource International, USA). The assays are performed according to the manufacturer's instructions. Results are calculated as pg cytokine/ml of culture medium, and then expressed as percent control.

Measurement of Intracellular cAMP

Intracellular cAMP is measured in LPS-stimulated monocytes isolated from whole blood by adherence. Whole blood (100 µl) is added to wells of a 96-well tissue culture plate and incubated at 37° C., 5% CO2, for 1 h. After this time, wells are washed twice with 500 ∝l RPMI 1640 (heated to 37° C.). Complete RPMI 1640 [RPMI 1640+5% (v/v) heat-inactivated foetal calf serum+1% (v/v) penicillin/streptomycin] containing 10% (v/v) LPS (final concentration 1 µg/ml) is then added to the wells (100 ∝l/well) and incubated at 37° C., 5% CO2, for 23 h. After this time, 100 µl caffeine (final concentration 0-100 µM) is added to the wells, and cultures are incubated for a further 1 h. Intracellular cAMP is then measured using the Amersham cAMP EIA system, according to the manufacturer's instructions.

Statistical Analysis of Data

Data is analysed using a one- or two-way completely randomized analysis of variance. If any statistically significant change is found, post hoc comparisons are performed using either Dunnett's two-tailed test or Newman Keul's test where appropriate. Data is deemed significant when P<0.05. Data are expressed as group means with standard errors.

The results show that the combination of caffeine and fexofenadine have synergistic and/or unexpected reduction or improvement of inflammation and associated symptoms as compared to the use of caffeine or fexofenadine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

Example 15

Caffeine/Cetirizine Suppression of TNF-Alpha Production Via Activation of Cyclic AMP/Protein Kinase a Pathway Following the abstinence period from caffeine-containing food and beverages, heparinized venous blood is to be drawn from healthy volunteers. Blood is diluted to diluted 1:10 with RPMI 1640 tissue culture medium containing 1% (v/v) penicillin/streptomycin (Gibco Life Technologies, Scotland). Briefly, 400 ∝l aliquots of diluted whole blood are pipetted into wells of a sterile 48-well plate (Nunc, Denmark). To each well, 50 µl of either RPMI 1640 (control), cetirizine (dissolved in RPMI 1640 to yield final concentrations between 1-10 µM cetirizine), or cetirizine/caffeine (dissolved in RPMI 1640 to yield final concentrations in culture of 10, 20, 50, and 100 µM caffeine and 1-10 µM cetirizine). Following a 2 h incubation at 37° C. in a 5% CO2 atmosphere, 50 µl of lipopolysaccharide (LPS) from *Escherichia coli* (serotype 0111:B4) is added to each well at a final concentration of 1 µg/ml. Cultures are then be incubated for a further 24 h at 37° C. in a 5% CO2 atmosphere. At the end of the incubation period, culture supernatants are removed, centrifuged at 15,000×g for 15 min, and stored at −20° C. until the ELISAs are performed.

Measurement of Cytokines in Tissue Culture Supernatants

TNF-α, IL-1β, IL-12, and IL-10 is measured using commercially available enzyme-linked immunosorbent assays (Cytosets, Biosource International, USA). The assays are performed according to the manufacturer's instructions. Results are calculated as pg cytokine/ml of culture medium, and then expressed as percent control.

Measurement of Intracellular cAMP

Intracellular cAMP is measured in LPS-stimulated monocytes isolated from whole blood by adherence. Whole blood (100 µl) is added to wells of a 96-well tissue culture plate and incubated at 37° C., 5% CO2, for 1 h. After this time, wells are washed twice with 500 ∝l RPMI 1640 (heated to 37° C.). Complete RPMI 1640 [RPMI 1640+5% (v/v) heat-inactivated foetal calf serum+1% (v/v) penicillin/streptomycin] containing 10% (v/v) LPS (final concentration 1 µg/ml) is then added to the wells (100 ∝l/well) and incubated at 37° C., 5% CO2, for 23 h. After this time, 100 µl caffeine (final concentration 0-100 µM) is added to the wells, and cultures are incubated for a further 1 h. Intracellular cAMP is then measured using the Amersham cAMP EIA system, according to the manufacturer's instructions.

Statistical Analysis of Data

Data is analysed using a one- or two-way completely randomized analysis of variance. If any statistically significant change is found, post hoc comparisons are performed using either Dunnett's two-tailed test or Newman Keul's test where appropriate. Data is deemed significant when P<0.05. Data are expressed as group means with standard errors.

The results show that the combination of caffeine and cetirizine have synergistic and/or unexpected reduction or improvement of inflammation and associated symptoms as compared to the use of caffeine or cetirizine alone, or added together, e.g., at least 2-50 times reduction or improvement, e.g., at least 2, 3, 4, 5, 6, 7, 8, 9, 10, 15, 20, 25, 30, 35, 40, or 50×, or any range or value therein.

While the present invention has been described with reference to the specific embodiments thereof, it should be understood by those skilled in the art that various changes may be made and equivalents substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method of treating symptoms of tumor necrosis factor-α (TNF-α) mediated inflammation by inhibiting TNF-α, as measurable using assays that measure inhibition of TNF-α levels in the blood, plasma or tissues; and wherein the TNF-α inhibition is not attributable to inhibition of histamine activity, in a mammal in need thereof, the method comprising:
    (a) administering to the mammal every 4-12 hours a TNF-α inhibiting pharmaceutically effective amount of a composition comprising:
        (i) a TNF-α inhibiting amount of caffeine as 20-500 mg every 4-12 hours; and
        (ii) a TNF-α inhibiting amount of an antihistamine selected from at least one of loratadine or cetirizine, or pharmaceutically acceptable salts thereof; wherein the cetirizine or salt is provided as 0.50-20.0 mg; and the loratadine or salt is provided as 5.0-50.0 mg; and
        (iii) a carrier or diluent; and,
    (b) determining that said effective amounts are sufficient to inhibit TNF-α as measured using a TNF-α inhibition assay that measures inhibition of TNF-α levels in the blood, plasma or tissues;
    wherein said TNF-α inhibition is not attributable to inhibition of histamine activity.

2. A method according to claim 1, wherein the composition is administered by a route selected from oral, buccal, cutaneous, nasal, parenteral, vaginal and rectal.

3. A method according to claim 1, wherein the composition comprises a mixture selected from the group consisting of a solution, an emulsion, a suspension and a powder.

4. A method according to claim 1, wherein the caffeine and loratadine comprise from about 0.01% to about 50% w/w of the composition.

5. A method according to claim 1, wherein the caffeine and loratadine comprise from about 0.01% to about 5% w/w of the composition.

* * * * *